United States Patent [19]

Rauscher et al.

[11] Patent Number: 4,889,526

[45] Date of Patent: Dec. 26, 1989

[54] NON-INVASIVE METHOD AND APPARATUS FOR MODULATING BRAIN SIGNALS THROUGH AN EXTERNAL MAGNETIC OR ELECTRIC FIELD TO REDUCE PAIN

[75] Inventors: Elizabeth A. Rauscher; William L. Van Bise, both of San Leandro, Calif.

[73] Assignee: Magtech Laboratories, Inc., Reno, Nev.

[21] Appl. No.: 120,914

[22] Filed: Nov. 13, 1987

Related U.S. Application Data

[60] Division of Ser. No. 775,100, Sep. 11, 1985, Pat. No. 4,723,536, which is a continuation-in-part of Ser. No. 644,148, Aug. 27, 1984, abandoned.

[51] Int. Cl.⁴ .......................... A61N 1/42; A61N 1/36;
[52] U.S. Cl. .................................. 600/14; 128/420 A; A61N/1/42; A61N/1/36
[58] Field of Search ....... 128/419 R, 420 A, 421–422; 600/9–10, 13–14

[56] References Cited

U.S. PATENT DOCUMENTS

| | | | |
|---|---|---|---|
| 4,153,061 | 5/1979 | Nemec | 128/420 A |
| 4,401,121 | 8/1983 | Rodler | 128/420 A |
| 4,556,051 | 12/1985 | Maurer | 600/14 |
| 4,654,579 | 3/1987 | Thaler | 600/14 X |
| 4,693,238 | 9/1987 | Jenadek | 600/14 |

*Primary Examiner*—Francis Jaworski
*Attorney, Agent, or Firm*—Thomas I. Rozsa

[57] ABSTRACT

This invention incorporates the discovery of new principles which utilize magnetic and electric fields generated by time varying square wave currents of precise repetition, width, shape and magnitude to move through coils and cutaneously applied conductive electrodes in order to stimulate the nervous system and reduce pain in humans. Timer means, adjustment means, and means to deliver current to the coils and conductive electrodes are described, as well as a theoretical model of the process. The invention incorporates the concept of two cyclic expanding an collapsing magnetic fields which generate precise wave forms in conjunction with each other to create a beat frequency which in turn causes the ion flow in the nervous system of the human body to be efficiency moved along the nerve path where the locus of the pain exists to thereby reduce the pain. The wave forms are create either in one or more coils, one or more pairs of electrodes, or a combination of the two.

20 Claims, 6 Drawing Sheets

Fig. 1.
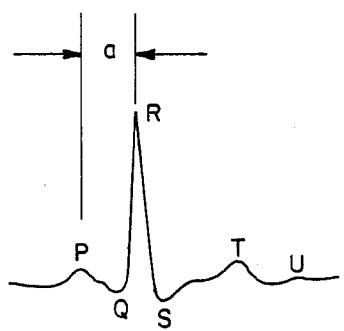
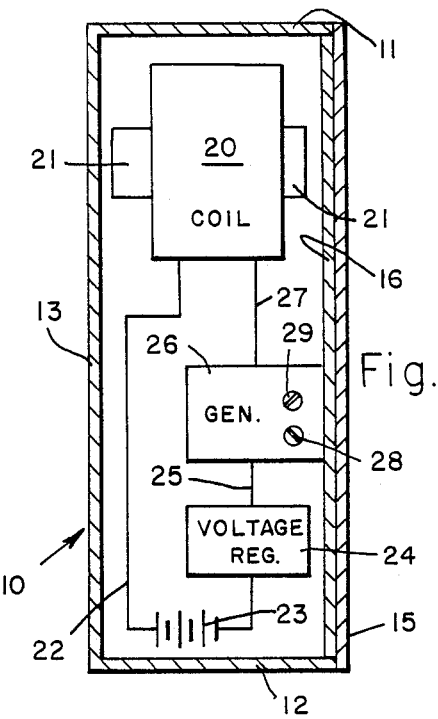
Fig. 3.
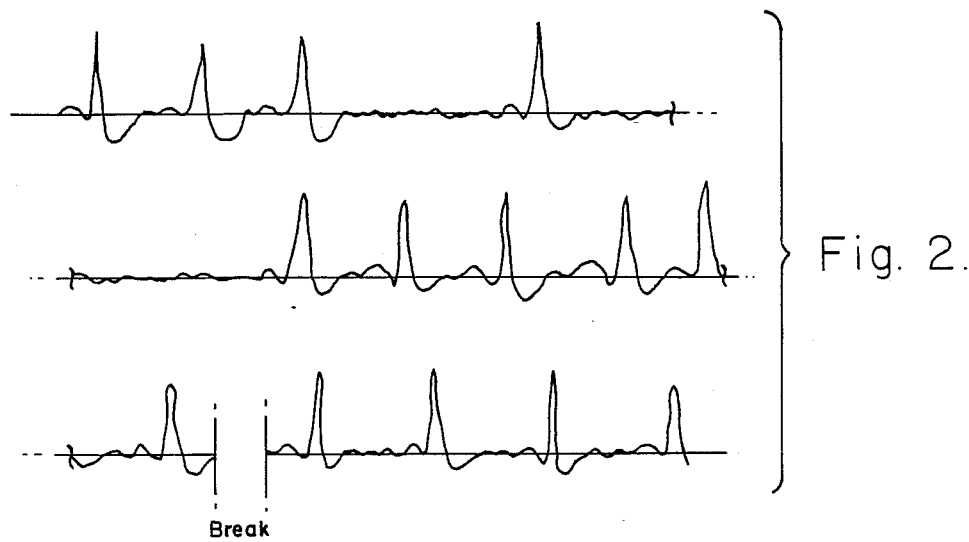
Fig. 2.
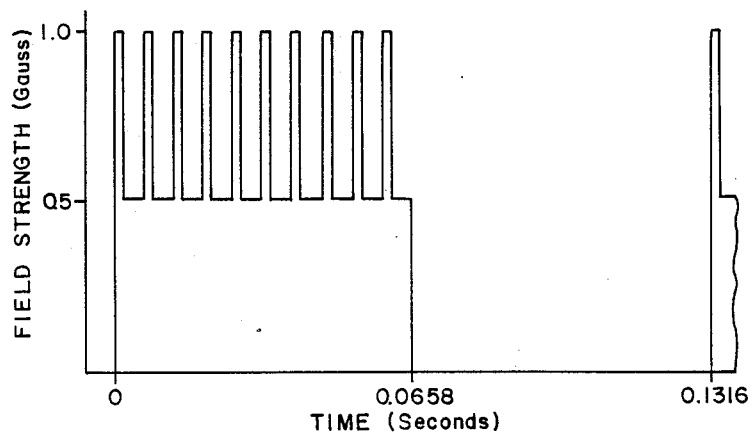
Fig. 4.

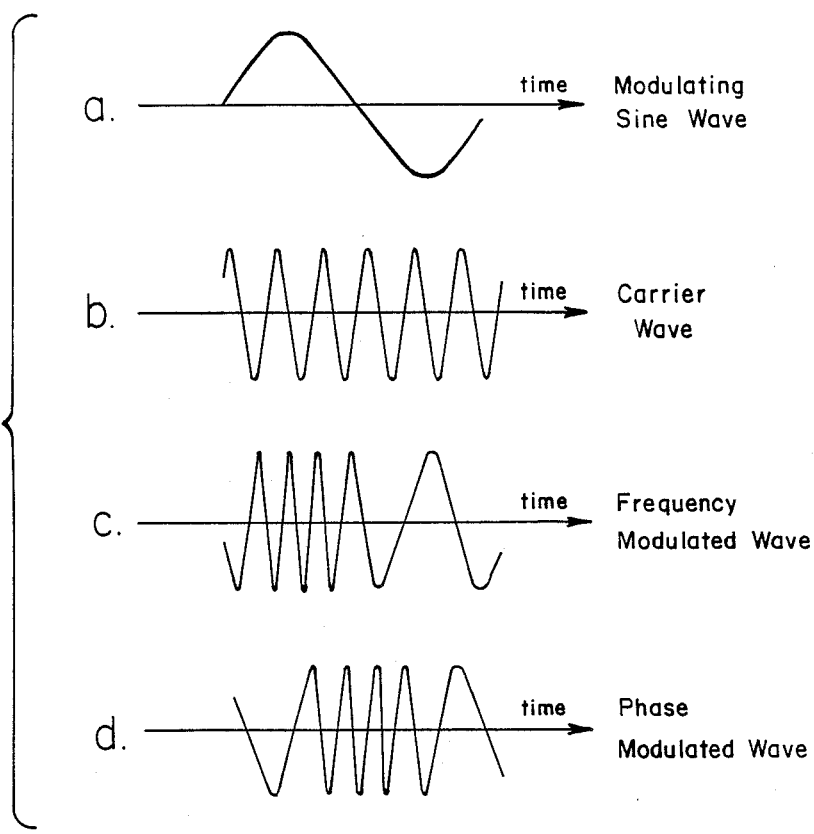
Fig. 8.
a. Modulating Sine Wave
b. Carrier Wave
c. Frequency Modulated Wave
d. Phase Modulated Wave
Fig. 9.
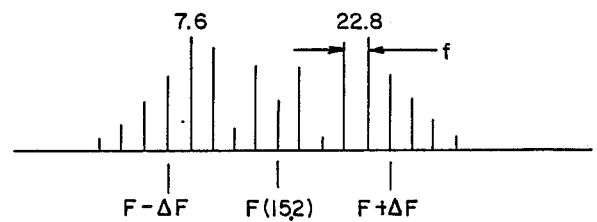
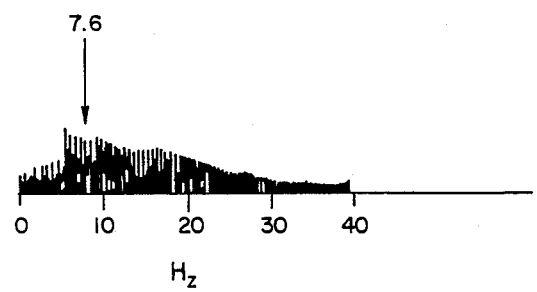
Fig. 10.

NON-INVASIVE METHOD AND APPARATUS FOR MODULATING BRAIN SIGNALS THROUGH AN EXTERNAL MAGNETIC OR ELECTRIC FIELD TO REDUCE PAIN

This is a Divisional of Co-Pending application Ser. No. 775,100 Filed on 9/11/85 and now U.S. Pat. No. 4,723,536, which is a continuation-in-part of application Ser. No. 644,148 filed on 8/27/84, now abandoned.

BACKGROUND OF THE INVENTION

1. Field of the Invention

This invention relates to an electronic apparatus which is capable of generating a magnetic field that is precisely tuned in order to interact with the brain and the heart in order to pace the heart and also to interact with the nervous system in order to counteract pain.

2. Description of the Prior Art

Arrhythmias and other cardiac problems are associated with abnormal pulse rates. Abnormal heart rates are usually associated with heart blocks. Severe heart blocks are treated with artificial pacemakers while incomplete or partial heart blocks are usually treated with drugs or they are just tolerated.

Artificial pacemakers include devices for timing electric impulses delivered to the heart through electrodes that are implanted in the heart. The timing device and the electrical impulses to the heart require a power source. In almost all of these pacemakers the electrodes as well as the timing means and the batteries are all surgically implanted beneath the skin of the patient. Because of this, even if the device malfunctions or if the batteries become spent, surgery is required to repair it.

Known artificial pacemakers stimulate the heart muscle directly with electric impulses that cause heartbeats. The impulses are provided at intervals that correspond to the heart muscle contraction rate. Artificial pacemakers of this category are wanting in several respects, among which are the discomfort and expense of surgery, that they put the user at risk to uncontrollable circumstances such as batteries exploding internally, malfunctions of the electronic impulses due to transmission sources such as microwave ovens and airport security devices and malfunctions due to faulty insulation in the lead wires. An implanted artificial pacemaker could also preclude some users from undergoing magnetic resonance imaging (NMR) as a diagnostic tool. Because of the very large fields and scan rate of NMR devices, they can interact with and affect the function of an internal artificial pacemaker, and conversely, an internal artificial pacemaker can distort the NMR data.

No prior art devices to counteract pains through appropriate magnetic signals are presently known in the prior art.

SUMMARY OF THE PRESENT INVENTION

The inventors have discovered that the beginning of the normal cardiac cycle and response to pain cycle originates in the mid brain and the hypothalamus with excitation of the Purkinje cells and is oscillatorily propagated to the heart or source of pain, respectively. In dealing with the heart, the SA node in the heart is the site of the electric excitation impulse which directly produces the contraction of the cardiac musculature. The electric excitation is propagated within the heart by specialized conductive tissues which include in addition to the sinoauricular node, the AV node, the bundle of His with right and left branches, the Purkinje cells and fibers.

One embodiment of this invention is an external, magnetic field generating device that regulates cardiac rhythm and character as well as a process for employing the device. The device may be worn near the heart, for example suspended from the neck or worn in the pocket of a user. It may be used only when needed, and it may be externally regulated. The device also is effective to regulate cardiac activity when worn near the occiput.

The device may be repaired or have its batteries or other energy sources changed without surgery and, particularly for persons with only partial blocks, the device of this invention may be worn only when the rhythm or character of the heart must be adjusted. The device of this invention is not affected by extraneous emissions from electronic devices.

The device of this invention includes means to produce an expanding and collapsing magnetic field the shape of which, when plotted against time, is in the form of a square wave. For an adult human the frequency is from about 7.15 to about 7.78 Hertz. The magnetic field produced by the device has a minimum strength at its poles of about 0.5 gauss. The square wave magnetic field must have a duty cycle of between 15% and 65%. The maximum strength of the magnetic field is limited only to avoid affecting others in the vicinity of the person wearing the device; it is not limited to any maximum value functionally. Affecting others can also be avoided by providing magnetic shielding or patterning the field with two or more coils so that the fields are directed toward the heart. Such shielding is available in the form of Mumetal, a trademark alloy having high magnetic permeability and low hysteresis and comprising iron, nickel, copper, chromium and manganese.

The term "square wave" is used herein as it is understood in the art, namely, a wave that is essentially in the form of an abrupt rise in value from a zero level followed by a period maintained at some maximum value followed by an abrupt decrease in value to the zero level. When plotting value against time, variations in the value produces a wave form made essentially of vertical and horizontal lines. Departures from absolutely vertical and horizontal lines through all portions of the wave are acceptable as long as the wave form of the magnetic field has an essentially square or rectangular form as understood by those skilled in the art.

An expanding and collapsing magnetic field at a frequency between 7.15 and 7.78 Hertz, preferably 7.6 Hertz, in the form of a square wave with a duty cycle between 15% and 65% will trigger responses in a human cardiac control system that cause a normal PQRSTU wave form in an electrocardiogram trace. The PQRSTU wave is the characteristic form of an electro-cardiogram trace and is referred to as a PQRSTU curve by those skilled in the art. It will be discussed in greater detail herein. Additionally, the magnetic square wave in the above mentioned frequency range will trigger those responses regularly and at normal intervals. In the device of this invention there is no need to produce a magnetic field wave form in the shape of a normal PQRSTU wave nor is there any need to pulse the square wave impulses in a sequence that duplicates the pulse rate of the person being treated. Rather, it has been found that continuous exposure to the square wave magnetic field having a frequency between 7.15 and 7.78 Hertz causes the human user's heart to beat in a normal PQRSTU wave and at normal intervals.

The frequency of the square wave magnetic impulses of 7.15 through 7.78 Hertz is effective for adult human beings. These frequencies may be varied for different mammals or for humans with large or small hearts and with characteristically different heart rates. The frequency should be about 6.18 times the normal pulse (in seconds of the user).

In the second embodiment of the present invention designed to treat pain, the magnetic field impulses generated by the device will be at two frequencies differing from each other by a factor of about ten. The frequencies are mixed to counteract pain. For an adult, a frequency of about 76 Hertz is superimposed on a square wave field having a pacemaking frequency of about 7.6 Hertz. The higher frequency impulses are only used during the duty portion of the lower frequency impulses. In addition, the higher frequency impulses have been found to cause a malfunctioning heart to stabilize to a normal heart rate more rapidly than if the lower frequency impulses are used alone.

The magnetic field impulses generated by the devices of the present invention do not completely override the normal physiologic mechanisms, but rather augment them. Under physical stress the pulse rate of one using this device will increase and while sleeping, the pulse rate will decrease, even though the device operates at a constant frequency. In general, when the device operates at lower frequencies, in the range from about 7.2 and 7.5 Hertz, it will cause a user to have a faster heart rate and when the device operates at higher frequencies, it will cause a user to have a slower heart rate.

The inventors have discovered that an expanding and collapsing magnetic field of precise shape and form influences the Purkinje cells and cardiovascular hemodynamics. One cluster of Purkinje cells is found in the AV node of the cardiac muscle and another in the cerebellum at the hypothalamic-pituitary axis. These regions of the body are known to be involved with pacing the human heart. However, until use of one embodiment of the device of the present invention, it was not known the Purkinje cells are apparently influenced by magnetic impulses of the character described herein. However, whether Purkinje cells or cardiovascular hemodynamics are involved in the operation of the device of this invention, it has been found, as will be demonstrated, that this invention is effective to regulate the pace and character of cardiac activity.

The device described herein reinforces this electrical activation and conduction system because by the time the impulses from the device reach the cardiac muscle, their frequencies match very well with the known propagation rate of the aforementioned excitable tissues. Thereafter, the imposed magnetic impulses reinforce and normalize the electrical conduction system.

DRAWING SUMMARY

Referring to the drawings for the purpose of illustration and not limitation, there is illustrated:

FIG. 1 is a typical PQRSTU wave produced by a normal human heart.

FIG. 2 is an electrocardiogram trace of a person with a defective heart function showing the trace before use of the device of this invention and after use of the device of this invention.

FIG. 3 is a schematic illustration partly in cross section of a device embodying this invention.

FIG. 4 is a plot of magnetic field strength vs. time illustrating the preferred wave form of this invention.

FIG. 8 is a representation of a modulating sine wave, a carrier wave, a frequency modulated wave and a phase modulated wave.

FIG. 9 represents a typical spectrum of an FM signal, where F is the carrier frequency and f is the modulating frequency. The example is given for the cardiac system.

FIG. 10 is representation of a human heart ECG in the frequency domain showing a bandwidth of 30.4 Hertz with the dominant power at 7.6 Hertz.

DETAILED DESCRIPTION OF THE PREFERRED EMBODIMENT

Figure 5:
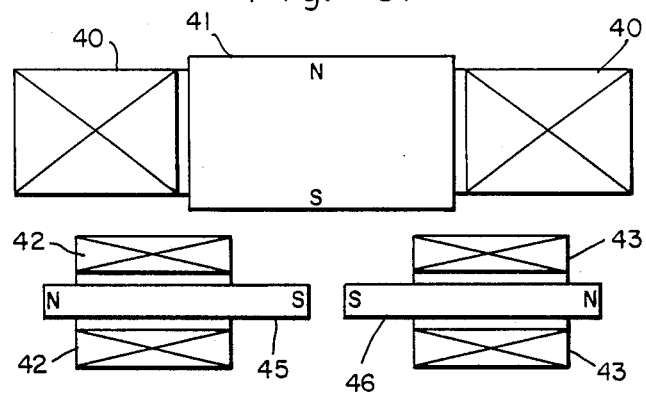
FIG. 5 is a schematic cross section view of another device embodying this invention.

1. Introduction: Description of Invention and its Application

This invention incorporates the discovery of new principles involving both linear and non-linear properties of biologic materials and inorganic semiconductor systems. By generating certain energies at a distance from as well as in the proximity of these materials or systems and at the same time optimally detecting their changes and emissions, unique new characteristics can be elicited and observed. Biologic as well as inorganic systems, when excited by external energies of specific, mixed or varying in a narrow range of frequencies, polarizations, wave forms and intensities, will have their own characteristics changed and in turn will change the characteristic of the energies impinging upon the system. Thus a characteristic transmitted energy impinging upon or traveling through a given self resonant system will stimulate the system to respond with a transmission of its own which is different from its transmission characteristic when undisturbed by the impinging energy. These two separate characteristic energies will interact synergistically producing not only greater effects at the disturbed local material sites but also will produce non local effects at other sites. The interaction of emitted energies from artificial sources and biological systems, if both are characteristically self resonant at some compatible fundamental or harmonic frequency results in the formation of an informational channel between the source and system. The informational channel in turn has a characteristic resonance compatible with the source and system. The channel frequency is able to modulate the interacting systems with diode-like forward-reverse voltage fluctuation. The channel is therefore a system frequency modulator.

Transverse and longitudinal wave and impulse energy interactions with in vivo and/or in vitro biologic material require precise tuning, magnitudes, wave shapes, mixtures, polarizations and durations in order to produce significant effects.

Living biologic systems exist and function through a series of physical-chemical-electro magnetic interactions. The physical and chemical interactions are fairly well understood by traditional science but a significant number of potentially beneficial advances in the medical arts have been ignored or considered of minor importance because of a lack of understanding of the non-linear interaction that take place between biologic material and electromagnetic energies. The areas of medical research which have been concerned with the electric or magnetic properties of living systems for the most part are based on the Hodgkin-Huxley model of the Giant Squid Axon and the sodium-potassium pump. This model predicts that biological material must interact with electric and magnetic energies in a linear manner, even though much research exists demonstrating non-linear effects do take place in biologic material as a result of electromagnetic interactions. The cardiovascular system is a notable example of a system that in some respects is highly linear, and in others behaves highly non-linearly.

The present invention is based on research and experimental evidence which indicates that at least three major components of a living system operate primarily on very non-linear far from equilibrium principles while yet retaining and utilizing their inherent linear qualities. The three components are the brain, the cardiovascular, and the nervous systems. This invention is based on research and test of devices which meet the criteria of a mathematical model which applies to a multi-system interaction and hence involves the description applicable to very non-linear systems. For example, we consider in detail here the neuronal FM information channel and the communications between the AM muscle-mechanical component for the cardiovascular system. The information channel interactions of a multi-system such as the cardiovascular system operate in an extremely non-linear self organizing manner. We can treat biological processes as linear only if we consider a small region of activity such as single, neuron firings within a small cross section of a limited area of the tissues. These limited regions of functional activities are able to be successfully described by the Hodgkin-Huxley, sodium-potassium pump model.

The inventors have developed and tested the herein described devices according to our mathematical model and these results and our model match very well. In order to clarify some of the physical-electric concepts involved with our invention, some of the key issues are described. It is well known that certain materials such as quartz, rochelle salt, and barium titanate exhibit piezoelectric qualities. That is if a mechanical stress such as a sharp impact or impulse is applied to a piezoelectric material such as quartz, a substantial electric potential impulse develops across two of the crystal faces of the material as a result of distortion of the lattice structure of the material. Conversely, if a fluctuating electric charge is placed across the two active crystal faces the piezoelectric material will mechanically oscillate at its characteristic vibratory rate which is determined by the size and cut of the crystal. The mechanical-electrical reciprocity makes this type of material useful as a timing device.

It is less well known that bone and collagenous material in biologic systems are not only piezoelectric but may, under the proper electrical-mechanical conditions function as semi-conductors and also as light-emitting diodes. The apatite crystal substance of bone is P type semi-conductor material, and the collagen fiber is N type semi-conductor material. The areas where these two co-exist is a PN junction diode which if forward biased with a voltage or induced current can emit an electromagnetic energy usually in the infrared region of the optical spectrum. With this information in mind, envision precisely formed magnetic impulses with shapes of varying phases and wave front envelopes emitted from an artificial source at precisely timed intervals penetrating and interacting with biologic material that has among other properties, piezoelectric qualities.

As is well known, magnetic fields will induce currents in conductors, and if we consider the field effects of the above described magnetic impulses on the capacitive, inductive, and resistive as well as the piezoelectric and semi-conductor properties of biologic material, it will immediately become apparent that the artificially emitted field will not only induce a reciprocity of field emission from the biologic material it is acting upon, but will also intermix with the re-emitted signal. The interaction of the emission-remission apparently behaves as an informational channel. The informational channel appears to be a frequency or phase shift modulated magnetically coupled system.

The information channel band widths are narrow with high "Q"s. The informational channel of the human cardiovascular system apparently has a band width of approximately 30.4 Hertz with a frequency swing of plus or minus 15.2 Hertz, and the second Bessel null is at about 7.6 Hertz. The human nervous system apparently has an informational band width of about 304 Hertz with a frequency swing of plus or minus 152 Hertz and the first Bessel component around 23 Hertz which represents the mix of the 7.6 and 76 Hertz generated signals. The human brain informational channel band width is approximately 3040 Hertz with a frequency swing of plus or minus 1520 Hertz, and a more complex mix of frequencies peaking between 70 and 123 Hertz.

It can be seen from the above that the informational channel of the human nervous system is about 10 times the band width of the informational channel of the cardiovascular system. The human brain informational channel band width in turn appears to be at least some 10 times the informational channel band width of the human nervous system where magnetic field impulses are concerned.

It is a well known engineering fact that in order for signals of given frequencies to be faithfully detected and reproduced that the receiving channel must have a band width at least 10 times the frequency of the highest emitted frequency which must be processed. Informational channels of biologic systems seem to need just the optimum band widths for high "Q"s at specific resonant frequencies and at the same time possess the inherent capability to be as free as possible from outside interference or "static". Narrow band FM is therefore the logical choice which nature evidently selected.

Although many higher frequencies than described herein can be utilized to produce various significant biological effects the present invention relates to non-invasive devices which emit magnetic pulses that can penetrate through and interact with biologic materials and potentially all systems of the body in what is known as the ELF/VLF frequency range. These devices operate at low intensities and except for the noted exceptions, without direct contact with the material affected. Through this effect, the present invention can enhance the ability of biologic systems toward a state of improved function in many areas of organic dysfunction.

The present invention is concentrated on improving functional effects upon cardiac tissues, excitable tissues, and neurological systems. Each organ of the body has a given electrical or electromagnetic characteristic with which a given wave form will resonate and affect the function of that organ. The key principles involved are as follows: magnetic fields generated at specific frequencies, and the harmonics of those frequencies, wave shapes, polarizations, or electric currents from cutaneously attached electrodes, will penetrate the system and stimulate specific and general nerves, and other parts of a biologic system either electrically, piezoelectrically, paramagnetically or chemically, or all in concert when certain biologic material resonant conditions are met. There are also variable and mixed frequency ranges and intensities of magnetic impulses and electric current impulses which can affect specific and general areas of biologic tissues.

The mechanism of pacing the heart with magnetic impulses is involved with oscillation of the Purkinje cell network in the right and left bundle branches of the bundle of His which then stimulate the fibers in the AV node up into the SA node and back to the cardiac muscle. The stimulation of the cells and corpuscles of Purkinje at the hind brain and medullan center dendrites of Purkinje cells can also be stimulated to produce pacing of the heart. Since the wave shape, frequency, pulse width, and rise-fall time of the magnetic field matches the QRS Complex of the human heart rate when the square wave impulses are transmitted through the chest wall but at a higher Fourier Bessel function of the muscle contraction frequency of the system, the Purkinje pacemaker cells are magnetically stimulated to initiate electrically the proper QRS interval. It has been discovered that the cardiovascular system specifically and the central nervous system in general behave as narrow band FM informational channels with AM components. The AM component of the cardiovascular system, for example, is the sinoatrial node excitation waves which produce the cardiac muscle contractions at normal heart rates. The SA node excitation waves are believed by traditional medical principles to be the origin of the pacemaking of the heart.

Specifically, the present invention eliminates the need to watch for the critical T-wave interval of the heart and eliminates the need to avoid applying the device at that time, as is necessary with all prior art pacemakers. This is because the magnetic field impulses stimulate the natural pacemaker cells and tissue at their natural higher frequency excitable rates. These higher rates then frequency divide down stepwise to the appropriate tissue excitation to the normal contractile rate of the whole muscle mass. Pacing the heart in this manner precludes the possibility of triggering the critical T-wave interval improperly. The cardiovascular system interprets this superimposed pacemaker impulse field as its own field and not a foreign field.

Other important factors involved in the pacing of the human heart with magnetic impulses are that material in the blood heme is paramagnetic and the vascular system is acoustically resonant at approximately the same frequency which can magnetically stimulate the Purkinje cells and other pacemaker cells. A paramagnetic substance is one in which the molecules tend to align themselves parallel to a magnetic field.

The magnetic 7.6 pulses per second field can be utilized to pace the heart system either at the chest wall or in some cases through the cranium so as to stimulate the hypothalamic and Purkinje processes two way feedback system to also provide a stable normal heartbeat.

It has also been discovered and substantiated by several tests conducted by the inventors that arrhythmias, tachycardias, bradycardias and atrial fibrillations can be corrected with local field intensities as low as 0.2 Gauss.

While it is known that the non-myelinated fibers involved in afferent human autonomic nervous system pathways concerned with blood pressure and heart rate control arise from the carotid sinus and the aorta, it has been discovered that the Purkinje cells behave as biological diodes (one way signal gate). The activated signals travel from the Purkinje cells in the heart via the vagus nerve through the medulla oblongata and pons Varolli up to the Purkinje cells of the cerebellum. From here the tendril fibers of the Purkinje cells (in the brain) relay "rectified" signals from the Purkinje process in the aorta. At the same time the efferent (traveling from the brain) myelinated fibers arise from cells located in the inter mediolateral columns of the spinal cord and the appropriate cranial nerves and route opposite "diodelike" (one way) signals into the medulla oblongata to the hypothalamus and finally the cortex via the limbic system from the corpuscles and cells of Purkinje. The cells and corpuscles when magnetically stimulated act as semiconductors with the "electronic gate" consisting of the junction of the molecular and granular layers of the cerebellum. The Purkinje cells and fibers are part of the biological material stimulated by magnetic field impulses.

The carotid artery in particular and the rest of the cardiovascular system in general have a common group of electrical and fluid dynamical characteristics based on the dimensions, materials and structures of the whole arterial system which yield a set of parameters suggesting that an ideal resonant frequency within the system is around 7 Hertz. The ejection of blood from the left Ventricle into the aorta causes a pressure pulse which travels upwards into the aortic arch then descends within the thorax on the left side of the vertebral column, passes through the aortic opening in the diaphragm finally dividing into the left and right common iliac arteries and thence divides into all the other vessels and systems involved with arterial blood distribution in these areas. The ejection of blood into the aorta thus causes a pressure pulse which travels in a forward direction until it reaches the first or iliac bifurcation where part of the pulse rebounds back toward the aorta. These two oppositely moving pulses can interact as in and out of phase waves. When these waves are in phase with each other, a standing wave is formed and investigation has shown that standing waves exist in the arterial system. The bounding pulse characteristic of most people with high blood pressure is an example of a distally located standing wave phenomenon of the arterial system.

Resonant frequency is determined by size, structure, shape, and material in analogy to the hydrodynamics of an acoustic system. Since the heme of the blood contains paramagnetic material, this material will tend to align parallel to and oscillate with the predominant magnetic polarity and frequency of external magnetic impulses which match the resonant frequency of the system. The inventors have found that the characteristic resonant frequency is near 7.6 Hertz. The Purkinje cell network propagating impulses at 400 cm/sec acting as a semiconductor diode-like electrical device with a switching rate around 7.6 Hertz senses the resonant frequency of the heme-blood vessels-magnetic field system condition and initiates the appropriate impulse-feedback system to drive the cardiac system smoothly. The stimulation of the Purkinje cells network in the right and left bundle branches appears to stimulate the atrioventricular node which in turn feeds back informational pulses into the right sinoatrial node. The pacemaker focus in the SA node now has informational entrainment as regular pulses which initiates finally the electrical spread of excitation waves to the entire muscle mass in an orderly manner. We therefore have found that the commonly held theory that the sequence of the muscle contraction process is the sequence of electrical stimulation dynamics is incorrect, and in fact, the electrical-dynamical process appears to occur in exact opposite steps to the muscle contraction process as outlined above.

The production of the magnetic field form that represent the QRST Complex and activates the proper cardiac firing of the same also involves expanding and collapsed fields emitted from a coil electrically energized by square wave pulses. Sharp expanding impulses and collapsing impulses are produced so that an uncritically damped mode after the PQ portion results. This output looks like the RST form in the magnetic field emission from the cardiac pacemaker but at rates which match the value of the second Bessel function, i.e. approximately 7.6 Hertz. The band width of the cardiovascular system is approximately 30.2 Hertz and the second Bessel function is at 7.6 Hertz. These emissions are transduced and rectified by the capacitive, resistive, piezoelectric elements of bone collagen, protein bound water, excitable muscle and nervous tissue in the intervening chest or cranial tissues that activates the myocardium through the action of the two sets of Purkinje cells. These tissues act electrically as a low pass filter when external magnetic impulses pass through them.

Figure 6:
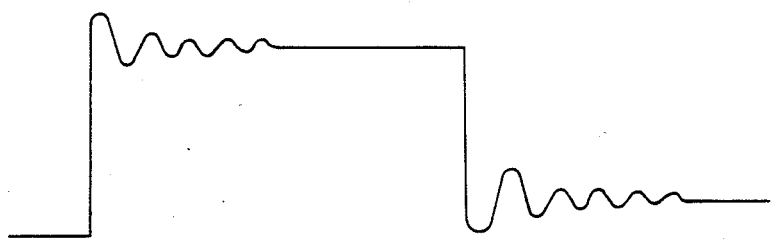
FIG. 6 is a wave diagram of a square wave pulse showing ringing.
Figure 7:
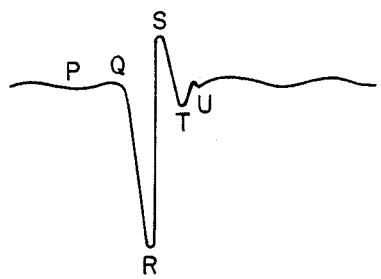
FIG. 7 is a wave diagram of a 7.34 Hertz square wave from a coil of a 100 kilohm input impedance displayed on an oscilloscope set at a trace speed of 10 milliseconds per division scale and resembling the PQRSTU type form of an EKG with a V-2 lead configuration.

The above written description is illustrated in FIG. 6 and FIG. 7.

2. Scientific Principles and Equations Supporting Invention and Experimental Verification Therefor This invention utilizes the theoretical constructs that involve the description of a nonlinear, non-equilibrium information system that is a coherent, resonant locked and a system of an infinite series of Bessel functions from an FM constant energy signal process.

Neuronal processes in the CNS, heart and brain are theoretically describable as a coherent "self focusing" informational channel which is composed of a series of harmonics represented as Bessel functions which are locked together at proper resonance when healthy pathways occur. The piezoelectric properties of bone and collagen as well as the neuronal pathways operate in concert to produce normal informational signals.

The inventors can definitely formulate nonlinear, dispersive properties in terms of pulse type eigenfunctions or soliton solutions. Soliton waves are said to be orthogonal in the sense that two or more crossing each other's path, essentially do not interact and hence do not distort or disperse. The phase velocity is obtained proportional to the square of the amplitude of such a system. The key to the soliton type phenomena is that soliton configurations arise so that the non-linear form balances the dispersive type mode in a "meta stable" or critically stable mode.

Certain parts of the biological-electrical system can be treated as a semi-conducting electrical system. Certain coherent collective electromagnetic phenomena are describable by a set of non-linear equations yielding solutions of energy propagation in which dispersion is balanced by re-coherence yielding solitary wave solutions. Such a model of neuronal/electrical activity can describe longitudinal neuronal information transmission which is characterized by the self-organizing properties described by Prigogine thermodynamics.

We apply this thermodynamical picture to describe systems that when a diode or diode array is properly connected to elements such as an antenna and a capacitor and the system placed so as to be exposed to random broad band noise, the noise can be rectified and stored in the capacitor as a unidirectional energy reserve. This comprises an example of a self-organizing system. Biological systems as well as this device employ these principles. For example, the actual electrically stimulated collective, coherent, solitary wave modes which proceed from a semiconductor substrate and diode-like array which are represented by the Purkinje cells and corpuscles as well as other neuronal cells, act in concert with nerve, bone and blood systems.

Low frequency radiations affect biological material and act as a systems narrow band FM informational system which utilizes almost constant energy input but contains very large informational channel capacity. These systems are examples of systems describable by the Prigogine far from equilibrium thermodynamics. The system described herein is an open, far from equilibrium one, which operates with a continuous energy flux. The energy flux in this case is both electro-magneto-dynamic as well as hydrodynamic and in its normal mode of operation is a system which loses very little energy. These systems are nonlinear and self organizing in that a small flux field perturbation can produce a large change of the system's state properties. The inventors have demonstrated that the Fourier Bessel equation which described the FM system describes an informational channel which is frequency modulated within the lossless channel of the soliton wave solutions to a set of magneto-electro-hydrodynamic equations. The waves going into and out of the heart must impedance match each other so that the system is relatively lossless between the present invention and the physical person.

In the conventional theory the wavelength of an electromagnetic signal of around 7.6 Hertz is inordinately large and hence would be seen as a wave so slowly changing in time as to not interact significantly with matter. Therefore, in general, electric field effects are minimal in the ELF (extremely low frequency—from less than 1 Hertz to 300 Hertz) region. On the other hand, magnetic impulses at ELF frequencies act as perturbations in the earth's steady state magnetic field and are "seen" by matter as impulse perturbations of this field. With the exceptions of portions of the visual, tactile and auditory systems, living organisms primarily utilize and generate frequencies in the ELF region. The intensities of these radiations are however significantly below threshold for thermal effects upon or in biological tissue. The reason such low intensities of pulsatile magnetic fields generated by external sources produce such dramatic effects on biological tissue and their processes is that they can be made to match the internal processing mechanisms of the biological tissue.

This matching of externally generated imposed fields to those utilized by the biological systems occur when proper impedance matching conditions exist.

In accord with the inventor's model, high intensity external signals may not impedance match well enough to produce phase shifting or soliton dispersion but may produce thermal agitation or noise and at extreme intensities, molecular bonds can be broken. The inventors can choose specific low frequency pulsed electric or magnetic signals which will induce magnetic pulsations that recohere and reinforce normal, biologic system functioning when these field forms are such as to be able to produce the normal signal modes in the desired tissue areas. In their clinical experience, the inventors have found a remarkably narrow range of frequencies in different individuals and in the same individual at different times in regard to the apparent characteristic pulsed emissions of given organ systems. That is the given pulsed wave signals which induce a given desired healthy biological function response on one person seems to be able to elicit the same response in other people. The inventors' formalism describes a structure of both the externally generated fields and the internally generated biological fields. The longitudinal (phonon) like modes composed of the Fourier Bessel series fine structured components comprise the soliton model.

The soliton model of biological signaling becomes useful in describing the various conditions of bioelectromagnetic processing. Tissue nonlinearities determine the dispersion and/or coherence of the various signal systems in the biological system or human body. Disruption or enhancement occurs because external signals transduced by the nonlinearities of the tissues form into Soliton like waves. These waves, then can modify and recohere processes which are too dispersive and hence reinforce normal neuronal or other signal paths. On the other hand these waves, at other frequencies, wave forms and intensities can increase dispersion and hence introduce disruption and biological damage in the system. The reason that pure magnetic impulses are useful in the application of modifying biologic tissue is because frequencies in the ELF range have their electric and or electromagnetic component modified by the biological tissue during the signal's excursion through the tissue so that it becomes a pure magnetic signal. Essentially, in the soliton model, tissue acts as a transducer device and longitudinal wave rectifier so that they transform waves which carry horizontal components into longitudinal wave components. Losses occur when impedance mismatching exists and other kinds of losses may also occur such as eddy current and hysteresis losses. Biological tissue is "transparent" to some ELF frequencies, therefore, frequency wave form and pulse repetition rate specificity is extremely critical to producing an effect within or on the biologic system under consideration. The effect of pulsed magnetic fields that interact with biologic material is extremely similar across a species. In the case of humans, the system's own informational channels react to the proper pulse fields as its own pulse field. Therefore, the reason biological matter can utilize square wave forms more efficiently is because of the ringing that occurs in these wave forms which produce a unique set of Fourier components. These components supply the complexity of structure of its electromagnetic field necessary to carry the needed bit rate in a biologic informational channel. Thus theoretically, the special ringing of biologic material is produced primarily by the piezoelectric qualities of bone and collagenous matter. FIG. 6 is a drawing of a square wave pulse showing the uncritically damped sinusoid ringing trails. When a pulse with a square wave form passes into biologic material which contains piezoelectric qualities, the square wave form induces a complex secondary delayed pulse in this material. The external square wave pulse and the induced complex delayed pulse together produce a wave form which appears very similar to the QRS complex wave. FIG. 7 shows the output of a 7.3 Hertz square wave modified by a simulation of piezoelectric biological material properties and it can be seen that the form resembles the PQRST complex.

These systems involve dynamic coherence and dissipation which gives their structure and energy constitution; all soliton phenomena is "dissipative". Processes can involve either static or dynamic stability and/or equilibrium. Non equilibrium states are maintained to create the conditions for no dissipative "loss less" conditions so that information is not disturbed or disrupted. The high bit rate is maintained because the FM process creates and utilizes an infinite number of locked resonant harmonics in the asymptotic limit. One needs to consider the Bessel equation rather than the Fourier equation since in the application to the human body, the inventors are considering that most organs and systems are best defined as spherical radiators. The skull and the heart can act as a spherical receiver/transmitter antenna. For example the Fourier equation can be applied to moving waves in a plane whether mechanical, acoustic, or electromagnetic, whereas the Bessel equation can be applied to processes which have approximately spherical symmetry and hence is more applicable to wave phenomena in organs. In some cases, as in local biological functioning, a plane or approximately flat surface excitation can be considered. Essentially, the Fourier equation represents a simpler form than the Bessel equation. One will find that in certain applications the Fourier equation will suffice for a formalism but in general the inventors will be dealing with the Bessel equation and its solutions. These solutions are of a specific form which are termed Bessel functions. In some cases we can express Bessel functions in terms of gamma functions. In the case of the Fourier equation the solutions are usually in terms of trigonometric functions such as sines, cosines, and in some cases hyperbolic functions.

It appears that the electrical and electromagnetic and magnetic human body functioning involves a complexity of wave function solutions that in general are not describable in terms of simple trigonometric functions but involve relatively complex series of waves. In fact no simple sine wave or other simple wave form will effectively interact with biologic tissue to produce either a functional enhancement or diminution. The inventors have utilized an uncritically damped square wave in which ringing and wave distortion by the local impedance of the material considered can be expressed as a complex series of trigonometric functions. Essentially, the Bessel formalism can be utilized to describe the wave envelope and amplitude modulated components with the envelope in which dispersive losses due to damping occur. Insulator blockage due to a material of high dielectric constant would produce such observable generated fields where frequency and wave forms were not optimum.

In a normally functioning biologic process a steady electric and magnetic process proceeds which is modified by sensorial, and motor glandular modification for different activities. In general, the electric, magnetic and electromagnetic processes operate in such a manner as to produce a steady state condition. This is accomplished when the damping or dispersive losses are balanced by recoherence produced by the nonlinearities of the system.

Biological systems and processes are highly nonlinear. This allows them to utilize highly complex and dispersive wave forms which have many Fourier/Bessel components. The only manner in which processes can function in a coherent and continuous manner is to be structured nonlinearly in their processing of energy such as electrical energy so that dispersive losses are overcome or recohered.

A demonstration has been achieved that the Korteweg-de Vries equation and the Bessel and Fourier equation are derived from a fundamental wave equation. The Korteweg-de Vries equation defines extremely well, the manner in which a non-linear term defines the "balances" or recoherence of a dispersive term. The solutions to this equation are well defined and are termed solitary waves or solitons. Although the original application for the Korteweg-de Vries equation was to hydro-dynamics systems, and many other systems involving wave phenomena, the inventors have demonstrated that they can formulate an analogous equation with equal success to electro-magnetic and magneto-dynamic phenomenon.

In fact, the biological "signal" and "communication process" involves electrical, magnetic, and electromagnetic energy which utilizes the complexity of the Fourier-Bessel wave components and the coherent resonances of the soliton wave form. Essentially, we can picture the biological system as a communication network which utilizes square wave like impulses (analogous in a sense to an on/off mode) to activate, diminish and utilize electro-chemical, biochemical and energy potential processes to produce and regulate a variety of biologic functions. These functions are performed in specific organs, cells, nervous tissue, etc. The form slope, size, structure and composition of such systems determine the manner in which information is processed, cohered, dispersed, etc. by their nonlinear mechanical, biological or electrochemical energy forms.

The wave equation for a series of single closely approximate sine wave impulses is given by the equation:

$$\frac{\partial^2 U}{\partial X^2} - \frac{1}{C_0^2} \frac{\partial^2 U}{\partial t^2} = 0$$

where $c_o$ is the velocity of the wave and the amplitude, U, is a function of space and time. The general solution to this equation is of the form $$U = \sum_{j=1}^{N} A_j e^{i(kx - wt)}$$

for a series of amplitude constants, $A_j$. The dispersion relation for the systems described by this wave equation are $k = v/c_o$ where k is the wave number given in terms of the wave length of $k = 1/\lambda$ and $v$ is the frequency.

In proceeding to demonstrate the relationship of this wave equation to more complex wave equations which describe impulse waves, square waves, coherent soliton waves, etc., one will have different dispersion relations. Systems which exhibit dispersion (such as in the Korteweg-de Vries equation or other Soliton equation), $d^2\omega/dk^2 \neq 0$, for $v = \omega/2\zeta$. If both diffusion and dispersion predominate in a linear or highly nonlinear system, then we can write a complex form so that $\omega(k) = \omega_1(k) + i\Phi_2(k)$. For phase velocity we can write $$C = \frac{R_e \omega(k)}{K}$$

In order to examine the fundamental relation of the Korteweg-de Vries equation and the Fourier-Bessel equation, we utilize a general dispersion relation. The inventors derived the Korteweg-de Vries classical soliton equation to the classical wave equation and have also derived the Fourier-Bessel equation from the classical equation. The inventors demonstrated the manner in which these equations are related to each other in a fundamental manner. These equations allow the inventors to describe the manner in which a complex electromagnetic signal can remain coherent in space and time as a soliton or instanton wave. The inventors solve both the classical and semi-classical equations which are applicable to the biological system. The key is that the Fourier equation applies to rectilinear plane membrane surfaces and is useful when the inventors consider an approximately small area of tissue and can approximate this surface as a flat plane. More applicable to the inventor's biological case is the Bessel equation which applies to circular or curvalinear membrane surfaces or radius or curvature $a_x$ and $a_y$. Hence we proceed from polar coordinates $(r, \theta, \phi, t)$. Let us now define a dependent functional variable as $z(r, \theta, \phi t)$. Then we have $$\frac{\partial^2 z}{\partial t^2} = C^2 \left( \frac{\partial^2 z}{\partial r^2} + \frac{1}{r} \frac{\partial z}{\partial r} + \frac{1}{r^2} \frac{\partial^2 z}{\partial \theta^2} \right).$$

Let us consider the case where the symmetry of z will make z independent of $\theta$ and we have the boundary conditions on z as $z(a, t) = 0$; $z(r, \theta) = f(r)$; and $$\left( \frac{\partial z}{\partial t} \right)_{t=0} = 0.$$

We term f(r) the deformation function. Let $z = T(t)R(r)$ where R(r) becomes the spatial variation function. We have:

$$\frac{1}{C^2 T} \frac{d^2 T}{dt^2} = \frac{1}{R} \left( \frac{d^2 R}{dr^2} + \frac{1}{r} \frac{dR}{dr} \right) = -u^2$$

which yields $$T = A \cos uct + B \sin uct$$

and letting B=0 for our second initial condition we determine R by setting $u = \mu r$ which yields the form $$u \frac{d^2 R}{du^2} + \frac{dR}{du} + uR = 0$$

This is Bessel's equation and we have the first solution for this form as $$R = CJ_o(u) = cJ_0(\mu r).$$

Since the Bessel equation is a second order equation, there is another solution which has a singularity at the origin and hence we rule it out. The boundary conditions require that $J_o(\mu a)=0$ and $U=a_n/a$ where $a_n$ is a root of the Bessel function $J_o$. We also have $$Z = C_n \cos\frac{a_n c}{a} tJ_o\left(\frac{a_n}{a} r\right)$$

We can examine the system in terms of FM (frequency modulation). In an FM system, no change in output power amplitude occurs and frequency is modulated and detected as a voltage. Fourier-Bessel functions encode amplitude in addition to the frequency encoding. Frequency is displayed into the time domain and can be converted into the frequency domain. Both modes are then able to be detected and analyzed. As body electrical functions communicate by neuronal functioning, a full Fourier spectrum is representative of amplitude. Therefore the biologic neuronal system can guarantee an FM signal containing a rich array of Fourier-Bessel components which transmit the necessary signal array to be detected and analyzed by other neuronal systems. Hence, we have a method to analyze CNS and organ signals which are information transmitters and receivers.

If maximum deviation and frequency variations are suppressed, inhibited, or magnified, then body function should be modified toward a diseased state. Some Fourier components would be seen as missing when abnormal ECG or neuronal activity is measured. The present invention is utilized to re-establish missing components and cancel unwanted components which may represent a "shorted" circuit creating chronic pain. A system with chronic pain may also be able to transmit useable and necessary components.

Thus when a set of neuronal and other impulses do not exist, i.e. amplitudes and frequency are not present as represented by their Fourier components, then non-optimum information transmission results and we may term this condition a diseased or injury condition. Receptor filter detectors and analyzers of the body cannot read these signals in such a manner as to function normally and efficiently.

The soliton model of biological signalling becomes useful in describing the various conditions of bioelectricmagnetic processing. Tissue nonlinearities determine the dispersion and/or coherence of the various signal systems in the biological system of the human body. Disruption or enhancement occurs because the external signal transduced by the non-linearities of the tissue form into soliton like waves. These waves, then can modify and recohere processes which are too dispersive and hence reinforce normal neuronal or other signal paths. On the other hand these waves, at other frequencies, wave forms and intensities can increase dispersion and hence introduce disruption and biological damage in the system.

The information transmission capacity is proportional to the band width which is "chosen" to match the needed Fourier components. FM systems require very little power expenditures in relaying information as frequency modulations. FM systems also are highly resistant to static or external energies of large magnitude which would normally interfere with an amplitude modulated system and is therefore optimum for biologic information transfer to linear muscle, tissue or organ components that respond to amplitude and intergenerate modulations.

Frequency modulation is a constant power process and the power of the modulated wave does not change as the degree of modulation changes. The frequency-domain representation of an FM wave consists of a carrier and sidebands spaced in frequency around the carrier. The spacing between frequency components is equal to the modulating frequency $f_n$. Theoretically, the FM waves contain an infinite number of sidebands. The sideband energy, however, falls off very rapidly outside the peak frequency deviation where the deviation is measured with respect to the carrier frequency. The amplitudes of the various frequency components, including the carrier component, change as the deviation changes. This is a consequence of the requirement that the total power remain constant regardless of the deviation.

The relative amplitudes of the frequency components are in the same relationship as the relative amplitudes of Bessel functions of the first kind. Bessel functions of the first kind are designated as $J_o$ or $J_n$ for $n=1,2,\ldots$. The complete characterization of the frequency component amplitudes is $$J_n\left(\frac{\Delta F}{fn}\right)$$

where n is called the order and represents the frequency component number (p=0 for the carrier, n=1 for the first sideband, etc.) and $\Delta F/f_n$ is called the argument and represents the modulation index. The modulation index, denoted as $\beta$, is defined as the ratio: peak frequency deviation $\Delta F$ divided by the modulating frequency f.

Bessel functions are the solution to Bessel's differential equation, just as the standard trigonometric functions, sine, cosine, etc., are the solution to differential equations.

The information of interest in FM is: the carrier frequency (F), the modulating frequency (f), and the deviation ($\Delta F$). The carrier frequency F is obtained by reading the spectrum-analyzer center-frequency dial and the modulating frequency f is obtained by calculating the frequency spacing between two adjacent components by use of the calibrated dispersion. The deviation ($\Delta F$) can, however, not be determinable directly. First, one obtains the modulation index from which the deviation is then calculated.

Transmission and reception of biologic signals require the proper band width about the carrier frequency to faithfully produce and detect the signal. To be a faithful transmitter or receiver the bandwidth needs to be at least ten times greater than the band of frequencies carrying the information to be transmitted or received. The power spectrum of Bessel nulls and Fourier components thus defines the sensitivity of the organism.

In FIG. 8 we represent various wave forms in the time domain. The top wave form represents an unmodulated sin x or cos x wave that can act as a modulator of a carrier wave, which is represented second from the top. The third wave form represents a frequency-modulated FM wave. We also represent a phase modulated PM wave. Full use of the Fourier power occurs at the second Bessel function for the cardiac system. We treat the informational channels of the biologic system in our model of this invention as describable in terms of frequency and phase modulations (FM/PM). The 1/t term is incorporated as the simultaneous but inverse function of the argument which is the modulation index. Biological informational channels therefore employ FM/PM as multi-tone FM with the muscle contraction AM "pilot" component at about 1.23 Hertz. This allows the downward stepwise frequency oscillation divisions at 7.6 Hertz to occur as sum and difference sideband frequencies.

In FIG. 9 we represent the frequency domain. In FIG. 10 we represent a typical spectrum of an FM signal, where F is the carrier frequency and f is the modulating frequency. The example is given for the cardiac system.

We deduce that the body information signal utilizes FM and relates to the piezoelectric effect of bone and muscle material. The hydroxyapatite-like piezoelectric impulses interacting with the CNS make up the FM informational signals which are the Bessel functions of the modulating frequencies. The mechanical oscillator-transmitter in biologic systems would be vibrations and stresses in the bone and collagen resulting from motions within and without the system. These stresses and vibrations in turn generate electrical impulses and waves which radiate within and without the system. The biologic receiver system primarily operates as a feedback detection system with the CNS and, particularly that the Purkinje cells in the mid brain area serve as efferent diodelike detectors with specific switching rates.

We can write the Bessel function of zero order, denoted by $J_o(x)$, and is given the power series $$J_o(x) = \sum_{k=0}^{\infty} \frac{(-1)^K x^{2K}}{2^{2K}(k!)^2} = 1 + \frac{x^2}{2^2} + \frac{x^4}{2^4(2!)^2} - \frac{x^6}{2^6(3!)^2} + \ldots,$$

which is valid for all "k" and even can be valid when "k" is not an integer and k! is the factorial k. This is for the Bessel equation initial conditions of $Y=1$, $dY/dX=0$ when $x=0$. We can utilize this form provided the series converges. The rate of convergence determines the number of terms we consider. We can term this series a "harmonic" series.

We can also write the Bessel integral in a bounded region $$J_o(x) = \frac{1}{2\pi} \int_0^{2\pi} \cos(x\sin\theta)d\theta$$

and for the asymptotic condition $x \to \infty$ we can write $$J_o(x) = \sqrt{\frac{2}{\pi x}} \cos\left(x - \frac{\pi}{4}\right) + e^{|Imx|} \phi\left(\frac{1}{|x|}\right)$$

where $$\phi\left(\frac{1}{|x|}\right)$$

represents "of the order of" for $|\arg x| < \pi$. We can see that there is a relation between the J(x)'s and the trigonometric functions.

In general we can write the expression for the $p'^{th}$ order of the Bessel function, $$J_p(x) = \sum_{k=0}^{\infty} \frac{(-)^K \left(\frac{x}{2}\right)^{2K+p}}{k!(p+k)!}.$$

For the Bessel function of the first kind of zero order, $$J_o(x) = 1 - \frac{t^2}{4} + \frac{t^4}{2 \times 4 \times 8} + \ldots$$

Also we can write $p'^{th}$ order Bessel function as $$J_p(x) = \sqrt{\frac{2}{\pi x}} \left\{ \cos\left(x - \frac{p\pi}{2} - \frac{\pi}{4}\right) + e^{|Imx|} \phi\left(\frac{1}{|x|}\right) \right\}$$

for $|\arg X| < \pi$. This form uses Sommerfeld's integral representation and the method of steepest descent for a fixed "p" and asymptotic approximation for $|x| \to \infty$. We use "p" as a positive integer for our present consideration and hence do not need to generalize to the appropriate definition of p! for arbitrary "p". If we need to use the Bessel expansion for arbitrary "p", we can use the expression for p! in terms of the gamma function as $$\Gamma(p+1) = \int_1^{\infty} x^p e^{-x} dx$$

for $p \geq 0$ which can we solve and Bessel functions and the circular trigonometric functions are related. For large "x" then we can neglect the $$\phi\left(\frac{1}{|x|}\right)$$

term. That is, for the larger argument, the closer the Bessel function resembles a decaying circular function. We can also write the trigonometric functions in the terms of the Bessel function as, $$\cos x = J_o(x) - 2[J_2(x) - J_4(x) + J_6(x) \ldots ]$$

and $$\sin x 2[J_1(x) - J_3(x) + J_5(x) \ldots ]$$

so that a sinusoidal function can be expanded in terms of a series of Bessel functions. Bessel functions are orthogonal.

We can write trigonometric functions in terms of exponentials. This kind of form is sometimes useful for expansion formulas. We can write $\cos x + i \sin x = e$ and use expansion formulas of the type $$e^{-ix} = 1 + x - \frac{x^2}{2!} - \frac{ix^3}{3!} + \ldots$$

We can write an expression for the FM spectrum wave as $$a = A\sin\left(2\pi Ft + \frac{\Delta F}{f}\sin 2\pi ft + \theta_o\right)$$

where "a" is the Bessel coefficient, F is the carrier frequency, "f" is the modulating frequency, A is the carrier amplitude, ΔF is the peak deviation, and ΔF/f is defined as the modular index. We expand this expression in terms of a set of discrete sinusoids which appear at the carrier frequency, F, and sidebands or on either side of the carrier and are spaced at the modulation frequency, f, apart from each other. Theoretically there is no limit to the number of sidebands for an infinite frequency distribution. The amplitude of the carrier and the various sidebands are determined by the product of the original carrier amplitude, A, and the value of the appropriate Bessel function. The order of the Bessel function corresponds to the sideband number denoting the carrier component as number zero. The argument of the Bessel function is the modulation index ΔF/f.

The amplitude of the carrier component is modified for the FM process by the factor $$J_o\left(\frac{\Delta F}{f}\right);$$

the carrier component of the modulated wave is smaller than the amplitude of the unmodulated carrier. In some cases, the carrier component can go to zero, and this is called a null carrier and occurs when $$J_o\left(\frac{\Delta F}{f}\right) = 0.$$

The Bessel zeros are used to determine the frequency deviation. The reason the FM process is a constant energy process is because energy is removed from the carrier and supplied to its sidebands, so that the energy of an FM wave is constant regardless of the degree of modulation. This is in contrast to AM where the carrier amplitude is constant and the modulation process adds further energy to the carrier wave. The process of body metabolism could not supply the rapidly varying energy component to utilize AM information processes. It is a fact that FM is a constant energy process that makes it feasible for the body to utilize such a system for its informational carrying capacity.

We can write an expansion for an infinite series of sinusoids with Bessel coefficients as $$a = A\left\{J_o\left(\frac{\Delta F}{f}\right)\sin(2\pi Ft + \theta_0) + \right.$$

$$J_1\left(\frac{\Delta F}{f}\right)\sin[2\pi(F + f)t + \theta_0] -$$

$$J_1\left(\frac{\Delta F}{f}\right)\sin[2\pi(F - f)t + \theta_0] +$$

$$\left. J_2\left(\frac{\Delta F}{f}\right)\sin[2\pi(F + 2f)t + \theta_0] + \ldots\right\}$$

We derived the values for the Bessel functions used in this patent from a plot of the first 8 orders of Bessel functions as shown in FIGS. 4–4a on page 85 of the text Spectrum Analyzer Theory and Applications—by Morris Engelson and Fred Telewski. A plot for each $J_p(t)$ where "t" is an arbitrary index for the Bessel function and can be given as ΔF/f.

The neuronal pathways and their specific biologic material utilize a relatively narrow band FM spectrum. The FM spectrum sideband spacing can be determined, for example, in the case where the carrier component goes to zero. This is called a carrier null and happens when $J_0(\Delta F/f) = 0$. The first carrier null occurs at a modulation index of 2.4, where the zero crossing of J(t) occurs.

For our pain treatment invention, narrow band FM modulation leads to a series determined in detail by two coupled Fourier Bessel equations with a time varying coupling "constant". The carrier frequency, F, has been determined experimentally to be about 70 Hertz and ΔF=150 Hertz. Experimentally, the modulating frequency, f, which results from a dual frequency beat frequency, is about 23 Hertz and therefore the approximate Bessel function argument is 2. The Bessel functions for n=1,2,3, . . . are $J_0(2) \sim 0.2$, $J_1(2) \sim 0.58$, $J_2(2) \sim 0.36$, and $J_3(2) \sim 0.14$, and the higher order Bessel functions are all approximately zero.

Now we determine the FM spectrum for the cardiovascular system as follows: the carrier frequency f, or f=15.2 Hertz, where the peak frequency of the Fourier spectrum of the ECG output is 7.60 Hertz for an average heart beat of 1.23 Hertz. The effective narrow band FM is ΔF=30.4 then the Bessel function argument or index of modulation is t=ΔF/f=2 where f is the modulation frequency f=15.2 Hertz.

From FIG. 10, with argument t=ΔF/f=2 we determine the values of the Bessel function $J_n$ argument 2 or $J_n$ (2). Then we have the values for $J_0(2)$ etc. as $J_0(2)=0.2$, $J_1(2)=0.58$, $J_2(2)=0.36$, $J_3(2)=0.14$, $J_4(2)=0.04$ and $J_5(2)=0$. and all the additional components of $J_n(2)$ for n≧5 are zero. The largest Bessel function component for t=2 accrues for J (2) or the second Bessel function for a Bessel function of the first kind.

Note that the carrier null or zero occurs for $J_0(\Delta F/f)=0$, for an index of modulations of ΔF/f=2.4, that is $J_0(t)=0$ for t=2.4. The index of modulation, t is a frequency ratio. The second Bessel null where $J_1(t)=0$ is at t=3.8, the 3rd for $J_2(t)=0$ is at t=5.1 and $J_3(t)=0$ at t=6.4. Note that 2.4~2 for the value of t. The carrier frequency, F, can vary its frequency in a linear manner for F−ΔF to F+ΔF where ΔF is normally called the peak deviation. This process is repeated every T seconds for f=1/T, where f is the modulation frequency.

The inventors have demonstrated the derivation of the Fourier-Bessel equation from the classical wave equation and have been able to derive to Korteweg-de Vries equation from the classical wave equation and the generalized dispersion relation. The inventors have found the soliton type solutions and related these in a fundamental manner to the Bessel series harmonics which represent information and operate in a near "lossless" manner. This formalism describes an informationally stable system of equations in which predominate dispersive losses are recohered. The FM informational process occurs in such a manner in the human body so that solitary wave pulses are monitored in a normal healthy system. The inventors will now outline the mathematical formalism for such a system in term of solitary wave physics. They proceed from three different but related formulations.

First, starting with Maxwell's equations and the continuity equation, second from the generalized dispersion relation, and third, from Laplace's equation or the classical wave equation. The inventors present this latter derivation and relate it to the second method, since they can demonstrate the most direct relationship between the solitary wave coherent process and the complexity of the Fourier-Bessel FM signal channel process. They consider either steady state or space-time variational conditions. Proceeding from the Maxwell equations and the continuity equation also lead to equations having soliton solutions. Solitons have solitary wave forms described coherent states which are collective such as phonon like acoustic modes and/or longitudinal collective modes. The inventors proceed from Laplace's equation which has been related to the classical wave equation earlier in this document. The inventors demonstrate the relationship between the classical wave equation and the Korteweg-de Vries equation. It should be noted that the Laplace form has many general applications, such as thermodynamic, electromagnetic, and gravitational phenomena.

The three-dimensional Laplace equation is written as:

$$\frac{\partial^2 U}{\partial x^2} + \frac{\partial^2 U}{\partial y^2} + \frac{\partial^2 U}{\partial z^2} = 0$$

where U represents a general wave amplitude as a function of the independent variables x, y and z.

The two dimensional form is:

$$\frac{\partial^2 U}{\partial x^2} + \frac{\partial^2 U}{\partial y^2} = 0$$

where U is now considered a function of x and y. The inventors can now define $y^2 = -c_0^2 t^2$ for $y = ic_0 t$ which can represent a temporal component for wave velocity, $c_0$. Upon substitution, the above equation becomes $$\frac{\partial^2 U}{\partial x^2} = \frac{1}{C_0^2} \frac{\partial^2 U}{\partial t^2}$$

which is the one-spatial-dimensional and time-dependent classical wave equation which has solutions of the form $U \sim e^{i(kx-\omega)}$. The point we make here is that we can consider these equation forms to represent waves.

Now let us return to the wave equation we proceeded from before. We have wave function $U(x,t)$ in three dimensions as $U(x,y,z,t)$ as $$\frac{\partial^2 u}{\partial t^2} - C_0^2 \nabla^2 \psi = 0$$

for $\nabla^2 \equiv \frac{\partial^2}{\partial x^2} + \frac{\partial^2}{\partial y^2} + \frac{\partial^2}{\partial Z^2}$ for the simple case of $\omega_0^2 = c_0^2 k^2$ and the temporal component is $ic_0 t$ for $c_0$ the velocity of wave propagation. Note that Laplace's equation is a subset of this equation where we have two components of space x,y and no temporal component. If we consider three spatial dimensions we can formulate the dispersion relation for $k^2 = k_x^2 + k_y^2 + k_z^2$. The standing wave solution in the one dimension is then $$A \, e^{i(kx-\omega t)}$$

for the incident wave $$A \, e^{-i(kx-\omega)}$$

for the transmitted wave.

The inventors use as a general dispersion relation $$K(w) = \frac{w}{w_0} - \frac{1}{w} D\left(\frac{w}{C_0}\right)$$

where that frequency $\omega(k) = c_0 k + D(k)$. The general wave equation for this general dispersion relation is the integral-differential equation $$S\nabla^2 u = \frac{1}{C_0^2} \frac{\partial^2 U}{\partial t^2} - \frac{1}{C_0^2} \frac{1}{2\pi} \int_{-\infty}^{\infty} \int_{-\infty}^{\infty} dw dt \left[ w^2 - W^2\left(\frac{w}{C_0}\right) \right] u(x,y,z,t) e^{iw(t-t')}$$

We will now proceed and consider one spatial dimension only. The first two terms are the usual classical wave equation, the group velocity, $V_g = 2\omega/2k$. The inventors consider a finite amplitude wave propagation in a media where the nonlinearity of propagation is characterized by an amplitude dependence of the phase velocity. The inventors expand the phase velocity, $v_\phi$, as $$v_\phi = c_0 (1 + \beta_2 U + \beta_3 U + \dots ).$$

Then we have the kinematic equation of the form $$\frac{\partial U}{\partial t} + C_0 (1 + \beta_2 U + B_3 u) \frac{\partial U}{\partial X} = 0$$

where higher order nonlinear terms are neglected so that we use $\beta_2$ and $\beta_3$ respectively to represent quadratic and cubic nonlinearities. The presence of a quadratic nonlinearity for $\beta_2 \neq 0$ and $\beta_3 = 0$ yields the one spatial dimension Korteweg-de Vries equation $$\frac{\partial U}{\partial t} + C_0 \frac{\partial U}{\partial X} + C_0 \beta_2 \frac{\partial U}{\partial X} + \gamma \frac{\partial^3 U}{\partial x^3} = 0$$

where in simplest analytic dispersion relation $W(k) = c_0 k + D(k) = c_0 k - c_0 \beta_2 k^2 - \gamma k^3$ defines $\gamma$ where the analytic dispersive relation $W(k) = c_0 k + D(k)$ for $D(k) = c_0 \beta_2 k = \gamma k^3$ the amount of dispersive losses $\gamma 2^3 U/2x^3$ are balanced and recohered by the quadratic nonlinearity term $C_0 \beta_2 2U/2x$ and hence the values of $\gamma$ and $\beta_2$ are determined to be such that losses are minimized in the FM channel. The value of $\beta_2$ is such that the solution to the wave equation is simply a solitary wave.

In the nondispersive case, $\omega=c_0k$, and for quadratic nonlinearity, where dispersive processes exist, these are self-focused by the recoherence of the wave due to the nonlinear processes in the system.

The solution to the above equation is a sinusoidal pulse in a nonlinear medium characterized by amplitude-dependent phase velocity of the form $\omega/k=v_\phi=c_0(1+\beta_2 U)$ where $\beta_2>0$ for a pulse of wave amplitude U traveling at greater than or less than the velocity $c_0$ with phase velocity, $v_\phi$. The reference time is $t_n=t-x/c_0$. If the initial sinusoidal wave pulses occur and reach the discontinuity distance of $x_n=x=c_0\alpha\omega\beta_2$ then we have $$U(x,t) \sim a\sin\omega\left(t - \frac{X}{C_0}(1-\beta_2 U)\right)$$

for $U\beta_2<<1$. If we do not have a discontinuity then we have the lossless Korteweg-de Vries condition for a longitudinally stable stationary solution, $$U(x,t) = \frac{3(v-C_0)}{C_0\beta_2}\operatorname{sech}^2\left[\frac{1}{2}\sqrt{\frac{V-C_0}{\gamma}}(x-V(t))\right]$$

for $\beta_2>0$ and for velocity $v>c_0$ if $\gamma>0$ and $\mu<c_0$ if $\gamma<0$.

The above solution for the first case $\gamma>0$ is the conventional soliton solution. The velocity difference $v-c_0$ is proportional to the amplitude of the soliton pulse. The product of the wave amplitude and wave width is proportional to $|\gamma|/c_0\beta_2$ for small dispersive losses and the spatial width of the pulse is proportional to $3\pi|\gamma|/c_0\beta_2$. The Korteweg-de Vries solution represents a periodic nonlinear stationary solution which has an infinite number of harmonics locked in phase and velocity. These sinusoidal pulses lock together at resonance and form a synoidal wave form.

The fact that there is an infinite number of harmonics allows the informational capacity of the system to be extremely large for a small amount of constant energy input in the wave. The synoidal (not restricted to sine wave forms exclusively) wave phenomena allow for extreme stability of the system when the infinite number of harmonics is locked into resonance moving at a reduced velocity, where $v<c_0$. Solitary waves or soliton-soliton interactions do not disrupt the synoidal process and hence neuronal processing utilizing a system like this in CNS processing does not, under normal conditions, disrupt or interfere with other informational carrying processes of the human body. That is, perturbations in informational processing between neuronal branches can occur producing small phase shifts but the general wave form and shape are not changed.

The Soliton wave amplitude variation occurring at a frequency, $v_s$, acts as a modulation frequency varying as a slow wave amplitude variation. Essentially that soliton wave acts as a pulse train which acts like an AM modulation of the FM signal. No actual system can be a pure FM system, produced by voltage changes, but has some AM components, which is produced by current changes. Then $v_s<<F$, the FM modulation frequency and $v_s$ is set by the optimally functioning system so that dispersive losses are balanced by the recoherence by the nonlinearities of the system so as if to hold dispersive losses to a minimum.

For the cardiac system, F is the modulation of 15.2 Hertz and the frequency $v_s$ may be associated with the 1.23 Hertz muscle contraction node or beat frequency of the human heart. Another manner to picture this situation is that the frequency $v_s$ is the amplitude envelope frequency of the FM informational channel which has a higher set of frequency harmonics than $v_s$ which is at the low end of the FM band and controls mechanical functioning of the system.

The soliton mode of AM like modulation does require some power need variation but is relatively constant as the frequency $v_s$ is relatively large and constant. The FM informational channel involves rapid variation of frequencies to produce a high bit rate of information transmission. The soliton wave modulation then acts to produce a reasonably lossless informational channel. The set of biological informational channels act in concert to organize processes in the various systems of the body such as the brain, heart, CNS, etc.

The AM component as the Soliton variation frequency produces the energy for producing muscle contraction. Some of this energy and information is derived from the Bessel Functions at the low frequency range around 1.23 Hertz (See FIG. 10). Also, this energy variation shows up and is derived from the Soliton frequency, $v_s$ giving pulsation to the longitudinal waves in the human informational system.

The system recoheres dispersive phenomena as represented as soliton wave forms as envelopes to the harmonic series. Self resonant, nonlinear and nonequilibrium, coherent phenomena can be treated in this manner, informational channels in biological systems represent "self-organizing" phenomena as this theoretical treatment suggest. These informational channels operate as a resonant locked "loss less" or dispersion free system in which the resonant forms are treated as an infinite series of Fourier Bessel components. Narrow band modulation implies that only the first leading harmonics need consideration and the high order term contributions are treated in the asymptotic limit. In the cardiac and CNS system, only the few orders of Bessel functions predominate and the rest of the harmonics are approximately zero.

The inventors have discovered that the macrostructure of the body such as the neural pathways, muscles, tendons and skeletal structures are emitting, modifying and/or receiving information which maintain or remodify their activity. These systems, the cardiovascular system, etc. interact and affect and are affected by the microstructure system such as Purkinje cells, heme, endocrine and hormonal secretions. Also the lymphatic system affecting and being the effect of the immunological and other body components and to act as a set of feedback informational loops which adjust and readjust these systems over time.

3. Detailed Apparatus of the Present Invention as Supported by the Above Scientific Principles and Equations It has been determined that a magnetic field generator with a minimum coil output at the poles of approximately 0.5 Gauss and a repetition rate between 7 and 8 Hertz and more precisely 7.6 pulses per second will correctly pace the human heart. The precise pulse rate may need to be varied by a small amount depending upon the condition of the individuals' cardiovascular system. The magnetic field can be emitted from a small coil through which a current is intermittently passed. The current is turned on and off by an integrated circuit timer chip such as an Intersil 7555. The chip can be powered by any appropriate power source such as a standard 9 volt 500 milli-ampere hours alkaline battery. The unit should have a voltage regulator chip such as Intersil 7663 chip. The generated field consists primarily of a square wave fundamental frequency and the harmonics thereof. The localized forward and back electromotive force (EMF's) induced in the coil as a result of the expanding and collapsing magnetic fields at the on pulse and off pulse initiations are important wave shaping factors of the magnetic field and are also critical parameters.

The repetition rate is highly critical for this application and will only pace the adult human heart within the range of 7.15 to 7.78 pulses per second (Hertz). The appropriate frequency to which the present invention must be set in each individual application requires a precise tuning and long term stability to within 1/100th of a Hertz once the device is matched to the user's cardiovascular system.

The magnetic impulses from a coil which will pace the adult human heart must be driven by square waves with a duty cycle between 15% and 65% with the ideal duty cycle falling usually at about 50%. The wave shape at the coil output as measured with the proper equipment should resemble the PQRST waves of the heart. The PQ portion should have a five millisecond duration at 50% duty cycle square wave input. As measured with another coil as a sensor, the portion of the output emission which would be analogous to the Q-wave should be inverted and with the RST segment also having a duration of approximately 5 milliseconds at the repetition rates given herein for pacing the human heart. The total duration of the emitted impulses and the critically damped wave train which follows should be approximately 20 milliseconds. The Q-wave is the initiation of the magnetic emission and the RST emission is an uncritically damped wave resulting from the collapsing magnetic field of the coil during the off cycle of the square wave. The measurement of these emissions should be taken from a one to two pound coil of a number 44 wire having a DC resistance of approximately 300 to 350 kilohms wound on a plastic spool of approximately 3" by 5" dimensions with approximately 3 turns of 10 gauge mu-metal foil core. The output of this coil is fed into the vertical amplifier of an oscilloscope with an input impedance of at least 1 Megaohm and a sensitivity of 200 millivolts/centimeter.

The biological processes involve specific geometric and electromagnetic parameters which are key to the maintenance of the systems proper resonance states. Such a system is like a tuned circuit with a very high Q and narrow band width and thus is sensitive to weak field detection, amplification and distribution. As with the chest wall, the skull and the cerebral tissue act as low pass filters where the transfer function on the RMS noise voltage is a function of the frequency and the band width. Our devices employ these principles in such a manner as to match band width, wave form and pulse duration to the biological system with which the present invention interacts. The inventors have applied the principles enumerated above in experiments which indicate that not only the cardiovascular system but the central and peripheral nervous systems as well as the autonomic nervous system behave in similar fashion.

Electric and/or magnetic current at specific mixed and varying rates and intensities either cutaneously or externally applied magnetically will produce fields which reduce or extinguish pain. Experimental results indicate that some chronic pain sufferers have been free of pain for periods of time in excess of two weeks to over two months after a single application of 30 minutes duration of the present invention. Frequencies of 7.1 to 8 Hertz on the lower end mixed with 70 to 78 Hertz and applied in specific manners to be described will produce an electro-anesthesia as well as normalization of nerve pathway impulses in people in chronic pain. Treatment has also been successful for cases of current injury pain. The fundamental frequency range of interest for the pain control embodiment of the present invention lies between 7.1 Hertz and 78 Hertz. The mixed frequencies of approximately 7.6 Hertz with a second frequency of approximately 70.25 Hertz and a total duration of approximately 20 milliseconds will promote pain diminution and healing effects on nerves, bones, teeth and muscles of the body when applied transcutaneously with at least three electrodes. In the use of the device for pain control through the emission of magnetic pulsed fields from coils, one emission is sufficient for certain applications, however, two coils are the optimum number but more may be used if necessary.

The pain reduction and prevention embodiment of the present invention operates on the principle of inducing dual magnetic and/or electric impulses with specific fundamental pulse repetition rates of about 7 to 8 Hertz with approximately a 50% duty cycle and a square wave form which is the treatment frequency of the neural pathways associated with the pain location. This repetition frequency is fine tuned within its range to duplicate the neuronal discharge rate of the offending neuronal pathway conducting the pain impulses. Simultaneously applied with the 7 to 8 Hertz treatment frequency is a 50% duty cycle square wave magnetic impulse between 70 Hertz and 78 Hertz. This provides the electro-anesthetic effect while treatment is in progress.

As with the pacemaker device, a timer mechanism is supplied by an integrated circuit ICL 7555 timer, however, the duty cycles must be the same, 50% for the lower frequency and 50% for the upper frequency. The critical mix frequency appears at between 23 and 40 Hertz.

When the origin of the pain is in the spine, the field is extended to 3 points on the patient's body as follows: one point above the area representing the origin of the production of the pain, and two points distally from the first point. The latter two points need not be any specific distance from each other when cutaneously applied. For example, for L-5 (lumbar spine vertebra 5 in medical terminology) the number 1 point is at T-7 (upper back) and the #2 and 3 points are in the right and left legs respectively. For example, if the radiation of the pain is down the right leg, the #1 point is a positive terminal and the #2 and #3 points are negative terminals. If magnetic pulsation alone is utilized, small solenoid or pancake coils are affixed to these locations. If electric as well as magnetic modalities are desired, the coils are affixed to the skin with conducting pads. The disadvantage of the conducting pads is that they cause sweating and over a period of time skin irritation will occur.

The device of this invention operates on the principle of inducing dual magnetic and/or electric impulses with specific fundamental pulse repetition rates of about 7 to 8 Hertz with approximately a 50% duty cycle and a square wave form which is the treatment frequency of the neural pathways associated with the pain location. This repetition frequency is fine tuned within its range to duplicate the neuronal discharge rate of the offending neural pathway, i.e., the neuronal pathways conducting the pain impulses.

When the origin of the pain is in the spine, the field is extended to 3 or possibly 4 points on the patient's body as follows: one point above the area representing the origin of the production of pain, and two points distally from the first point. The latter two points need not be any specific distance from each other. One of these points must be at a minimum of about 12 inches away from the uppermost positive emitter point when electric field impulses from skin electrodes are used. Where the origin of pain is at L5 in the spine, the #1 point is at the upper back and the #2 and 3 points are in the right and left legs respectively. The radiation of the pain is down the right leg.

The #1 point is a positive emitter and the #2 and #3 points are negative emitters. If magnetic pulsation alone is utilized, small solenoid or pancake coils are affixed to the locations. The coils need not be at an approximate 12 inch distance from any other, and in some cases, a single coil emitting the dual frequencies at a pain location may be sufficiently effective. When two or more coils are utilized, the spatial proximity of the coils is limited only by the degree of their mutual inductance coefficient of coupling factor which would limit the effectiveness of pain control and treatment. If electric as well as magnetic modalities are desired, the coils are affixed to the skin with conducting pads. The disadvantage of the conducting pads is that over a period of time skin irritation will occur.

The coils are constructed so as to deliver two sets of pulsations simultaneously. The second set of pulsations, is about 10 times the treatment range: i.e.; 70 to 78 Hertz. These pulsations deliver an anesthetic effect only during the time that the device is in use. The therapeutic pulsations of about 7 to 8 Hertz are designed to have a long lasting effect persisting after the device is removed. The duty cycle of the anesthetic frequency is the same as the duty cycle of the treatment frequency.

When the origin of the pain is not in the spine (i.e. the head and/or brain stem) the placement of the emitters is adapted to the specific problem.

Experiments have been performed with placement of electrodes on a woman in her forties with chronic lower back pain and sciatica radial primarily to the right side. This pain responds to the nerve pathway magnetic resonance induced by the therapeutic device of this invention. The placement was determined by clinical and magnetic data indicating that the focus of pain production was at the L-5 level. X-rays corroborate this diagnosis insofar as discohgenic disease at the L-5 interspace is indicated.

In another treatment process, the inventors placed transcutaneous electrodes on the facial area when treating nerve inflammation caused by dental caries. The anesthetic frequency of 70 Hertz is mixed with the treatment frequency of 7.34 Hertz. The time of use depends on the time of treatment. In the case of dental work usually 15 minutes ahead of the treatment period is recommended before dental work is done. In headache, 15 minutes is sufficient in one case which was studied by the inventors.

4. Detailed Description of the Preferred Embodiment of the Cardiac Pacemaker and Pain Treatment Devices FIG. 1 illustrates a typical PQRSTU curve or trace made by a cathode ray tube or strip chart recording using an electrocardiogram device. Various characteristic parts of the curve are assigned the letters PQRSTU as illustrated. Each of the letters PQRSTU identifies either the top or the bottom of a transition point in the curve. If connections to electrodes are reserved the curve can be upside down from the way in which it is shown in FIG. 1 and still be a useful curve.

One of the most useful parts of the PQRSTU curve for diagnosis is the time interval between the P point and the R point. This interval is indicated as "a" in FIG. 1. A normal heart has about 0.16 seconds in the "a" interval. An "a" interval of 0.18 seconds is not desirable and an "a" interval of greater than 0.18 seconds indicates some degree of cardiac block.

Of course, a trace of a series of PQRSTU curves will clearly indicate other things, such as pulse rate, skipped heartbeats and problems involved with specific regions of a heart.

A device embodying this invention was constructed to produce an expanding and collapsing magnetic field having a maximum force of 2.0 gauss, a square wave form, a dual frequency of 7.6 Hertz and 76 Hertz, and a duty cycle of 50% for the low frequency and 25% for the high frequency. The device was constructed within a box having dimensions of approximately 4 centimeters wide, 5.3 centimeters long and 1.9 centimeters deep. One side of the box has a mu-metal shield to diminish magnetic impulses emanating away from the user. In the experiments described herein the device was held to the left of the sternum of the user's chest with the south pole against the chest. The device was suspended from the user's neck with a nylon cord. The user was afflicted with a partial AV heart block in that approximately one of each seven heartbeats was skipped and sometimes two beats in a row were skipped. The user's heartbeat also was irregular in the portions of the PQRSTU curve were not normal. The user was an 83 year old subject whose physical activity was somewhat restricted as a result of her cardiac condition.

With a practicing physician observing the procedure, the subject was connected to an electrocardiograph and a series of her PQRSTU traces were continuously recorded on strip chart paper. The tracings illustrated in FIG. 2 are not a complete record. The complete strip charts were taken over a period of several hours and are too long to be reproduced in FIG. 2. However, the traces illustrated in FIG. 2 are characteristic of the recorded trace. Before using the device of this invention, a beat was skipped about once in every six to ten heartbeats, several consecutive beats were skipped frequently, and the interval between the peak of the P curve and the peak of the R curve varied from approximately 0.19 to 0.22 seconds. After the device of this invention was put into operation and a stabilizing period of approximately 30 minutes elapsed, no heartbeats were skipped and the P-R interval stabilized to approximately 0.16 for every beat.

The objective data summarized in FIG. 2 were confirmed by the subjective response of the user who felt better after the device of this invention was put into operation. Her subjective response was that she felt less fatigued and her anxiety caused by skipped heartbeats, that were occasionally perceptible to her, disappeared.

In FIG. 2 the beginning of the curve illustrates the series of PQRSTU traces made with the subject at rest and in a stable condition. The electrode configuration was Lead III precordial, with polarity to strip chart recorder reversed so that the cardiac wave complex appears upright. At the point of the "Break" illustrated in FIG. 2, the above-described device was suspended from the subject's neck and in contact with her chest. An immediate effect on her PQRSTU traces was not perceptible but within five minutes no heartbeats were skipped although the interval "a" had not yet stabilized. By the time 30 minutes elapsed the subject's trace was as illustrated after "Break" in FIG. 1. No heartbeats were skipped and the "a" interval was regularly 0.16 seconds.

The subject had previously been diagnosed as having coronary artery disease, mitral valve prolapse and postural hypotension. Previously, ECG records taken at a hospital showed her heart rate at 60 beats per minute, rhythm NSR, P-R interval 0.22 seconds, QRS interval 0.08 seconds, ST-T wave abnormalities and a 1 degree AV block.

Prior to the testing reported above the subject had been using the device of this invention for five weeks and had experienced and subjective relief described above. To develop objective data, the device was removed from the subject for about four hours, after which the ECG record represented by FIG. 2 was started. The record showed that at that time her P-R interval varied between 0.19 and 0.22 seconds, her QRS interval was about 0.08 seconds and her rate was 77 beats per minute. The ECG was continued without using the device of this invention for about another 15 minutes, after which the device of this invention was placed to the left of the subject's sternum.

Within 18 minutes after use of the device was begun the subject's P-R interval stabilized to 0.16 seconds and her heart rate was reduced to 74 beats per minute. The QRS interval remained at 0.08 seconds, which is considered normal.

After 40 minutes the subject's heart rate was 68 and all other parameters remained stable.

When the device of this invention was again removed from the subject her parameters remained stable for several hours. This observation suggested that the device of this invention stimulates normal physiologic means of pacing the heart rather than imposed electric impulses to the heart muscle, and has the benefit of apparently reeducating the user's body to function normally.

FIG. 3 illustrates a device embodying this invention. The device of FIG. 3 includes a container 10 having a top wall 11, a bottom wall 12, one wall 13 to be worn adjacent a user's chest and one wall 15 to be worn away from a user's chest. Wall 15 is clad with a layer of mu-metal 15. The container 10 also has sidewalls, not numbered, to form a complete enclosure.

Within container 10 there is a wire coil 20 surrounding a core 21 that is made of mu-metal or other material, that is quickly magnetized by the flow of electric current through coil 20 and has its magnetism quickly collapse when no current flows through coil 20.

Lead 22 connects one end of coil 20 to battery 23 which has its other pole connected to precision voltage regulator 24 and then through lead 25 to a dual function square wave generator 26 that causes current to flow through the circuit completed by lead 27 to coil 20 at intervals which are adjustable from about 7.20 to 7.75 Hertz for the lower frequency and from about 72 to 77.5 Hertz for the higher frequency. An adjustment means such as potentiometers 28 and 29 is accessible through a wall of container 10 and connects to means within timing switch 26 to adjust the frequency of the cycle of the expanding and collapsing magnetic field.

In the embodiment of the invention in which both a high frequency cyclic field and a low frequency cyclic field are used, the same coil and core may be used to generate both fields or separate coils and cores may be used.

The various elements of the device are firmly connected together and to the interior of container 10 by means not shown but known to the art.

FIG. 4 is one plot of slightly more than one complete cycle of magnetic field strength against time developed by the device of FIG. 3. The high frequency waves have a duty cycle of about 25% and the low frequency waves have a duty cycle of about 50%. High frequency waves are created only in the active portion of the duty cycle of the low frequency waves. Thus, while high frequency waves are present they have a duty cycle of 25%. The field strength of the high frequency waves is substantially equal to that of the low frequency waves. The effect of the high frequency waves is to change the character of the wave form of the low frequency waves.

FIG. 5 represents another very effective embodiment of the invention. The device of FIG. 5 develops array patterned magnetic impulses that can be directed toward both the heart and the hypothalamus while directing a corresponding weak field in other directions. The device of FIG. 5 includes a flat coil 40 surrounding a mu-metal core 42. Flat coils of this type are known to the art as pancake coils.

Positioned below pancake coil 40 are cylindrical coils 42 and 43. Within coils 42 and 43 are mu-metal cores 45 and 46.

When the coils are connected in series to a common source of electric energy the magnetic flux emanating from the device is a resultant that forms a flux pattern that concentrates flux in certain regions surrounding the device. By placing the device at an appropriate location on the user's chest the concentrated flux patterns will be directed toward the heart and hypothalamus and the effect of the magnetic flux will be magnified.

The leads to the various coils are conventional and not illustrated. In the preferred embodiment the coils are connected in series but they may be connected in parallel or independently wired as along as the timing of current flow will produce the correct wave forms in the correct phase with each other.

Figure 12:
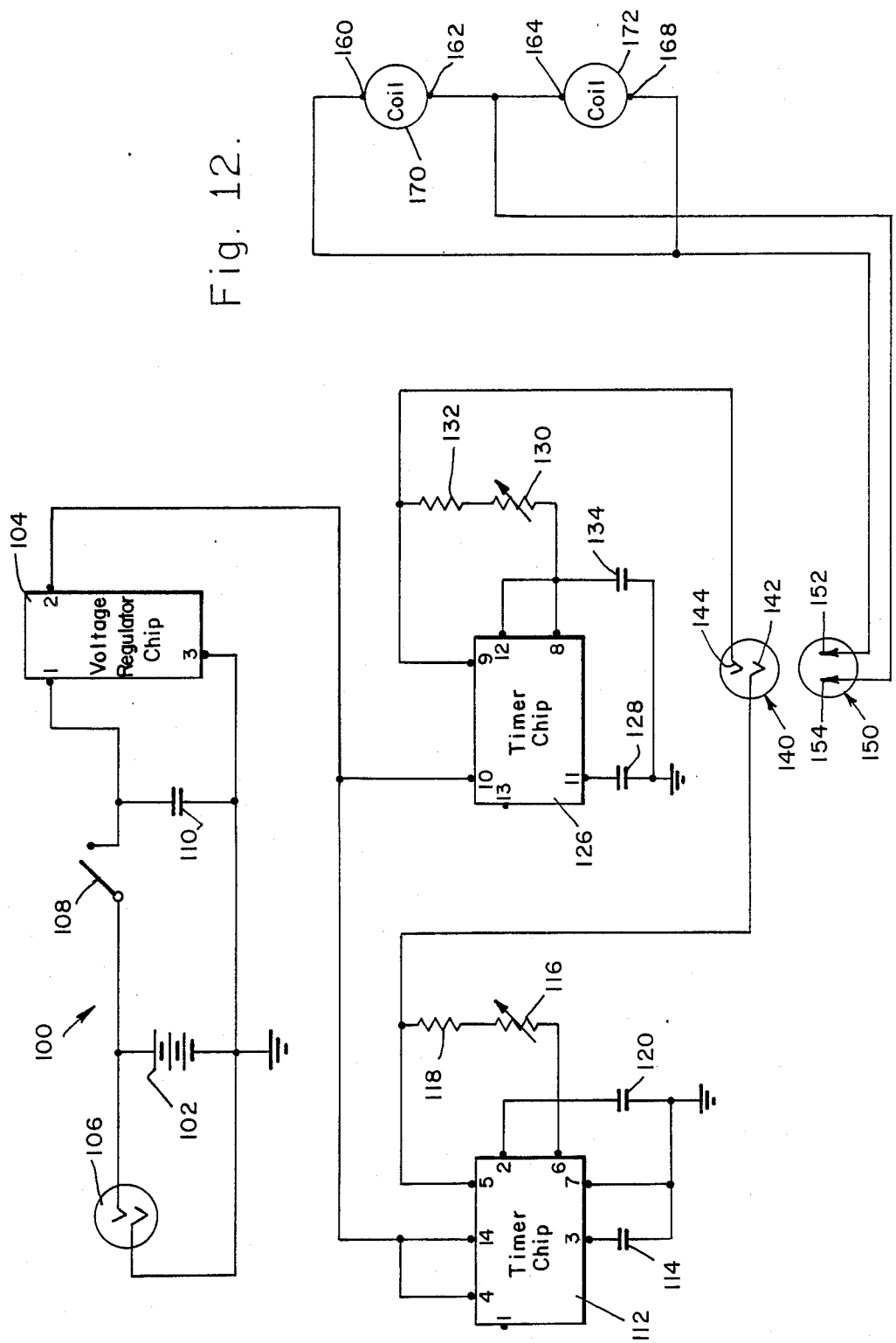
FIG. 12 is a circuit diagram of the embodiment of the present invention used to counteract pain.

The pain control circuit 100 is shown in FIG. 12. A battery (such as a 7.2 volt 500 milliampere hour nickel cadmium battery) 102 is connected to a three terminal voltage regulator 104 such as a 7805-1 ampere 5 volt rated regulator. The positive end of the battery is connected to terminal 1 of the regulator. Terminal 3 of the regulator is connected to the negative terminal of the battery and also common return to ground. An optional phono jack 106 is connected to the battery 102 in the event a rechargeable battery is used. The circuit also contains and on-off switch 108. Connected in parallel with the voltage regulator, also through terminals 3 and 1 is a 0.047 microfarad capacitor 110 which is needed to suppress power surge spikes. The output terminal of the voltage regulator is terminal 2 from which +5 volts of electricity emanate. The power goes into a dual timer regulator chip such as a 7556 Intersil timer chip. The first timer chip 112 has terminals 1, 4, 14, 5, 2, 6, 7, and 3. Terminal 1 is not connected. Terminals 4 and 14 are connected in parallel and are the power supply leads into the first timer chip. Terminal 3 is connected to a 0.01 microfarad bypass capacitor 114 which is useful for suppressing spikes and avoiding latch-up. Terminal 7 is connected to common ground and back to the negative terminal of the battery. Terminals 2 and 6 are connected in parallel and are routed through a 500,000 ohm 10 turn potentiometer 116. Also included in the circuit is a 500 ohm one half watt fixed resistor to avoid the timer frequency from going too high. Terminals 2 and 6 are also connected to ground through a 1 microfarad 35 volt DC capacitor 120. The combination of the 1 microfarad 35 volt DC capacitor 120 and the 500 ohm fixed resistor 118 and 500,000 ohm variable resistor (10 turn potentiometer) 116 determine the repetition rate of the output signal. The output signal comes through terminal 5 into the first end 142 of the output jack 140. The frequency output of this terminal is adjustable between 5 and 9 Hertz at a 50 percent duty cycle. Second timer chip 126 has terminals 13, 10, 9, 12, 8 and 11. Terminal 13 is not connected. Terminal 10 is connected to the power supply from the positive voltage emanating through the voltage regulator 104. Terminal 11 is connected to a 0.01 microfarad bypass capacitor 128 which is useful to suppress spikes and avoid latch-up. Terminals 12 and 8 are connected in parallel and are routed through a 100,000 ohm 10 turn potentiometer 130. Also included in the circuit is a 500 ohm one half watt fixed resistor 132 to avoid the timer frequency from going too high. Terminals 12 and 8 are also connected to ground through a 1 microfarad 35 volt DC capacitor 134. The combination of the 1 microfarad 35 volt DC capacitor 134 and the 500 ohm fixed resistor 132 and 100,000 ohm variable resistor (10 turn potentiometer) 130 determine the repetition rate of the output signal. The output signal comes through terminal 9 into the second end 144 of the output jack 140. The frequency output of this terminal is adjustable between 50 and 90 Hertz at a 50 percent duty cycle. The output jack 140 is connected to an input plug 150 which has two lead wires 152 and 154. The first lead wire 152 goes into one lead 160 of a coil 170 and into a second lead 168 on coil 172. By way of example, these coils 170 and 172 can each be a 240 ohm resistance type coil with a mu-metal core. The other lead 154 of the input plug 150 goes into second lead 162 of coil 160 and into first lead 164 of coil 172. The second lead 162 of the first coil 170 and the first lead 164 of the second coil 174 are connected together. Also, the two coils are connected in parallel.

In operation, the two coils are energized with a current flow proportional to ohms law which holds that current is proportional to voltage divided by resistance. The two potentiometers are set by means of a frequency counter readout connection placed at the output jack 140 wherein the first timer chip frequency is approximately 7.35 Hertz and the second timer chip potentiometer is adjusted so that the second timer chip frequency is approximately 70 Hertz. Individual settings of frequencies of the timers are then fed into the input plug of the coil. When the coils are so connected, the coils will emit a magnetic field. This magnetic field is measured by a magnetic detector placed adjacent to one or both coils. When the circuit chips are thus connected into the coil, their respective frequencies will vary from the setting of 7.35 and 74 Hertz respectively by + or − approximately 1 Hertz + or − 3 Hertz. This occurs because of the thickness of the square waves intermixing. There will be in phase and out of phase current lags and leads which reflect back into the timing mechanism of both chips. The signal from the detector is then fed into a real time spectrum analyzer and the analyzer range between 0.06 Hertz to 100 Hertz is observed to examine the fundamental frequency of the first and second timer outputs. If the first Fourier spike is at 7.35 Hertz and the second spike is at about 74 Hertz, no further adjustment is needed. If the spikes do not show these respective frequencies, the two potentiometers are adjusted until the frequencies are achieved. In addition, when examining the spectrum analyzer display, the intermix frequencies between the two spikes must be kept about 23 Hertz in order not to affect the human heart. If these two desired frequencies cannot be achieved without producing intermix frequencies above about 23 Hertz, then the low end frequency can be set below 7.35 Hertz in order to achieve intermix frequencies above 23 Hertz. After satisfactorily completing the adjustments, the device is now set for application. Through use of this embodiment, each magnetic coil will produce about 5 Gauss at each of the poles. The combined resistance of the coils must be about 120 ohms in order to produce the 5 Gauss output and have the proper intermix wave shape.

In the case of lower back pain with a locus of L-5, and sciatica radially down the right leg, the placement of the coils are as follows. The north pole of one coil is placed slightly below the right knee and at the nerve exit point on the inside of the leg. The other coil is placed approximately at the T7 level, but with the south pole facing toward the patient's spine. This treatment configuration is left on the patient for approximately 30 minutes after which period of time the coil at T7 is removed. The lower coil is left there for an additional 15 minutes and then removed. The above treatment treats the radial sciatica. For the L5 pain, the coil used on the leg is placed directly over L5 and the other coil is placed at T1. This treatment schedule is once again performed for 30 minutes, at which time the top coil is removed and the lower coil run for 15 minutes. This should eliminate both pains.

In general, the south or negative pole (which induces negative ion current) is used for treating extremities away from the brain and the outer coil is used at the highest convenient point near the brain with the north or positive pole (which induces positive ion current) toward the spinal column at the level of about C3.

The above application using the coils is expedient for treatments below the neck. When treating pain above the neck, transcutaneous electrodes must be substituted for the coils in order for the magnetic fields not to adversely affect the patient's brain. For treatment of dental pain, transcutaneous electrodes must be used and are attached as previously described. The electrodes are used in place of coils because we do not wish to influence the person's brain with these magnetic fields. There are two electrodes substituted for the two coils shown in FIG. 12. The setting for the potentiometers are the same as previously described. It is possible to have multiple positive and multiple negative electrodes each in parallel. The treatment time if dental work is to be performed is 15 minutes to 20 minutes before dental work is begun and left on, if feasible, during the dental procedure. The electrodes should be left on for about 15 minutes after the dental work is done and then removed.

If dental work is not to be performed, then the treatment time is approximately 1 hour.

Figure 11:
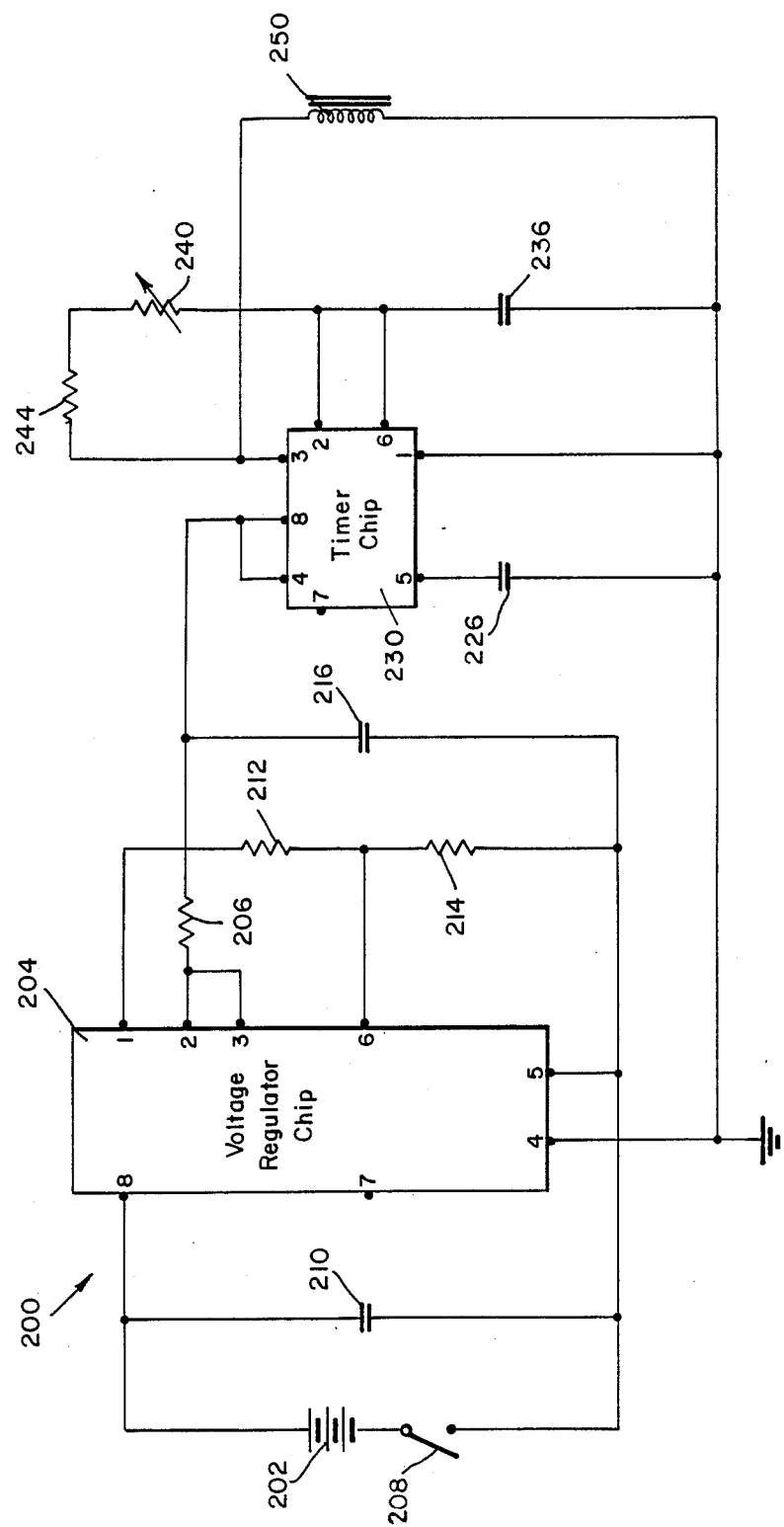
FIG. 11 is a circuit diagram of the embodiment of the present invention used to pace the human heart.

The Circuit for Pacing the Heart 200 is shown in FIG. 11. Initially we have a power source 202 such as a 9 volt 500 milliampere hour battery which can be rechargeable (in which case an optional phono jack recharger is included as previously described in the pain control circuit) or nonrechargeable. This battery 202 is connected to a precise voltage regulator chip such as in Intersil 7663 Integrated circuit. As illustrated in FIG. 11, this chip has 8 terminals. The positive terminal of the battery is connected to terminal 8 of the voltage regulator chip 204. The negative or common return to the battery is connected at terminals 4 and 5. A 0.047 microfarad spike suppression capacitor 210 is placed in parallel with the circuit. Terminal 7 of voltage regulator chip 204 is not connected. Terminals 2 and 3 are jumpered together and connected to a current limiting resistor 206 which can be a ¼ watt 150 ohm resistor. This in turn is connected to a voltage divider network which is composed of a 10 megaohm resistor 212 at the high end and 2.2 megaohm resistor 214 and variable resistor 215 which is a 25 turn 1 potentiometer at the low end. The three resistors are divided by a connection to pin 6. The positive output from the voltage regulator chip comes through terminal 1 and connects to the voltage divider and current limiting network just described. This entire network has a 0.01 microfarad spike suppression capacitor 216 connected in parallel to the output of voltage regulator. The regulated voltage leaving the voltage regulator is approximately 8.5 volts which enters a low current drain Intersil Timer ICL 7555. This chip 230 has 8 terminals as shown in FIG. 11. Terminals 4 and 8 are connected in parallel and receive the positive output voltage from the voltage regulator chip. Pin 7 is not connected. Terminal 5 is connected to a 0.01 microfarad bypass capacitor 226 and then connected to the ground return. Pin 1 is connected to the common return ground. Terminals 2 and 6 are jumpered together and are routed through a resistor control network composed of a potentiometer 240 which can be a 1 megaohm, ¼ watt 10 to 25 turn potentiometer and the 10 kilohm fixed resistor 244 to keep the oscillator frequency from going too high. Pins 2 and 6 are also connected through a 0.1 microfarad timing capacitor 236 to ground. Pin 3 is the output terminal which is routed to a coil 250 which contains a DC resistance. By way of example this can be a 15 kilohm solenoid coil with mumetal pole pieces. The other end of the coil is connected to common ground. In general, a fifty percent duty cycle is required. When connected in this manner, the Intersil 7555 timer chip has a 50 percent duty cycle. A circuit such as this one using a 500 milliampere hour 9 volt battery and a 15 thousand ohm solenoid coil will draw about 150 microamperes of current at 7.60 Hertz. This yields a useful life of approximately 138 days of continuous use. In practice the useful life has been about 60 days due the variations in shelf life age of the batteries sold as "new".

In operation, the pacemaker circuit is precisely set for the timing of the individual patient and ideally should be at 7.6 Hertz for most patients. Setting is performed as follows. A suitable frequency counter is connected to the output and ground across the solenoid coil and the potentiometer 240 is adjusted to within 1/100th of a Hertz to 7.60 Hertz. The apparatus is then placed over the patient's chest and in line with the patient's heart. For males, the preferred embodiment generally is that the south pole of the coil faces the heart. For females, the preferred embodiment generally is that the north or positive pole of the coil faces the heart but needs to be determined during ECG and pacemaker adjustment on an individual patient. In order to prescribe the precise frequency for a given patient, the patient's ECG during both resting and hyperventilation must be taken in order to determine the condition and character of the person's heart. If the patient's heart is not paced within a few minutes after the device is placed against the heart, and during the ECG recording, then the control potentiometer is turned in one direction or the other until proper pacing is observed.

The two circuits described above are representative of the two primary accomplishments of the present invention, namely to control pain and to pace the heart. Any multiplicity of comparable circuits are within the scope of the present invention provided they achieve the following results. For pain reduction, the lower frequency must be about 7.35 Hertz, the upper frequency must be about 70 Hertz, and the intermix frequencies must be above 23 Hertz. If the intermix frequency cannot be achieved above 23 Hertz with these settings, the lower frequency may be set between 7 and 8 Hertz and the upper frequency must not fall below 70 Hertz nor above 77 Hertz in order to achieve an intermix frequency in excess of 23 Hertz. For greater efficiency, the minimum magnetic output at the poles of the coils should be at least 5 gauss although magnetic outputs of 2 gauss will produce desirable results if the treatment period is extended. The duty cycle of the circuit must be 50 percent in order operate properly. For the pacemaker device, the circuit must produce a range of frequencies between 7 and 8 Hertz and must have a duty cycle between 40 and 60 percent. The minimum output at the poles should be at least 0.5 Gauss. The wave shape is dependent upon the coil configuration and DC resistance. Therefore, any coil which produces the wave form displayed in the PQRSTU form as shown in FIG. 1 is suitable for pacing the human heart. This is because the collapsing and expanding fields from the coil approximates the QRS shape of the heart as shown on an ECG. This is achieved through the parameters set forth above. The above described circuits produce a magnetic field wave shape of this form when the field is measured as above described.

Figure 13:
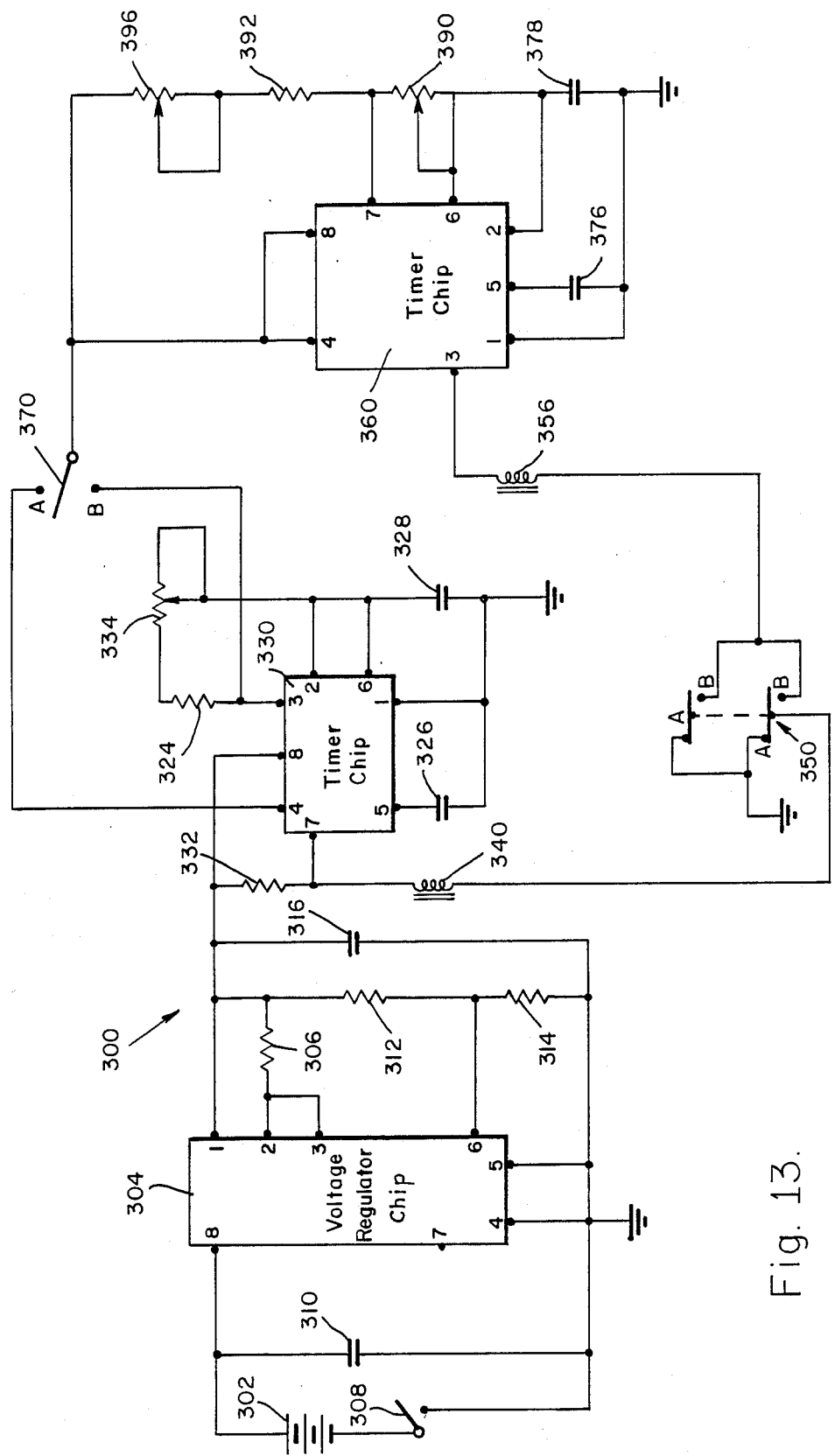
FIG. 13 is a circuit diagram of the embodiment of the present invention used to both pace the human heart and also used to counteract pain.

The present invention can also be embodied in a dual circuit 300 as shown in FIG. 13 which creates all of the above set forth parameters in order to both alleviate pain such as angina pectoris and pace the heart. Once again, the circuit begins with a power source 302 such as a 9 volt 500 milliampere hour battery which can be rechargeable or nonrechargeable. An optional phono jack recharger is included in the circuit using a rechargeable battery, as previously described for the pain control circuit. The circuit contains an on-off switch 308. This battery 302 is connected to a precise voltage regulator chip 304 such as a Intersil 7663 Regulator. As illustrated in FIG. 13, this chip has 8 terminals. The positive terminal of the battery is connected to terminal 8 of the voltage regulator chip 304. The negative or common return to the battery is connected at terminals 4 and 5. A 0.047 microfarad spike suppression capacitor 310 is placed in parallel with the circuit. Terminal 7 of voltage regular chip is not connected. Terminals 2 and 3 are jumpered together and connected to a current limiting resistor 306 which can be ¼ watt 150 ohm resistor. This in turn is connected to a voltage divider network which is composed of a 10 megaohm resistor 312 at the high end and 2.2 megaohm resistor 314 and multiturn potentiometer 1 resistor 315 at the low end. The two resistors are divided by a connection to pin 6. The positive output from the voltage regulator chip 304 comes through terminal 1 and connects to the voltage divider and current limiting network just described. This entire network has a 0.01 microfarad spike suppression capacitor 316 connected in parallel to the output of the voltage regulator. The regulated voltage leaving the voltage regulator 304 is approximately 8.5 volts and is applied to two timer chips which separate the ICM 7555 timer chips. The first portion 330 is the same as the heart pacer circuit except that with the first timer chip 330, the output from the battery enters the two terminals 4 and 8 which are jumped together and further enters terminal 7 via a 10 kilohm ¼ watt fixed resistor 332. Terminal 5 is connected to a 0.01 microfarad bypass capacitor 326 which is connected to ground along with terminal 1. The output at the point of connection from the 10 kilohm resistor to terminal 7 connects to a solenoid coil 340 of 15 kilohms which is routed via a double pole double throw switch 350 either to ground ("A" side) or pin 3 ("B" side) of the second timer chip 360 via another 15 thousand ohm solenoid coil 356. Terminals 5, 1, 6, 2, 3, 4 and 8 are identically connected as in the heart pacemaker circuit. Terminals 4 and 8 additionally routes to a single pole double throw switch terminal 370 and terminal 3 routes to the other ("B") side of the single pole double throw switch terminal 370 and then to a 500 ohm ¼ watt fixed resistor 324 and then to a 1 megaohm, 10 to 25 turn potentiometer 334 and then a 0.1 microfarad timing capacitor 328 and then to ground Terminals 2 and 6 are also connected to ground via capacitor 328. The switchable terminal of the single pole double throw switch 370 connects to pins 4 and 8 of ICM timer chip 360. Output pin 7 from first timer chip 330 routes through a 15 kilohm solenoid coil 340 through one centerpole of the double pole double throw switch 350 and then (through "B" side) to a second 15 kilohm solenoid coil 356 and then into output pin 3 of second timer chip 360. When the double pole double throw switch is in the "A" position, the output from both solenoids 340 and 356 go to ground. In timer chip 360, terminal 1 connects to ground. Pin 5 contains the 0.01 microfarad spike suppression capacitor 376 to ground. Terminal 2 is routed to terminal 6 and routed via a 0.1 microfarad timing capacitor 378 to ground. A 50 kilohm multiturn potentiometer 390 is connected between pins 6 and 7. Pin 7 connects to a 10 kilohm ¼ watt fixed resistor 392 to prevent dead ending and to 100 kilohm 10 to 25 turn potentiometer 396. Pins 4 and 8 of the second chip are also connected the other terminal of this 100 kilohm potentiometer.

In operation, as a pacemaker and pain alleviation device, both the single pole double pole switch 370 and the double pole double pole switch 350 are turned to the "A" position. Timer chip #1 (chip 330) is set to 7.60 Hertz with a 50 percent duty cycle and timer chip number 2 (chip 360) will be set at 70 Hertz via the 100 kilohm potentiometer and a 25 duty cycle is effected with the 50 kilohm potentiometer adjustment. In this A position, the 7.6 Hertz coil impulses from Timer A are routed normally to ground as is the 15 kilohm coil connected to timer chip 2.

When the two switches are thrown to the "B" position, timer chip #1 (chip 330) is adjusted at 7.35 Hertz as with the pain reduction embodiment and timer number 2 (chip 360) is adjusted to the 70 Hertz frequency and the duty cycle adjusted for 50 percent. Measurement are performed as previously described in order to achieve an intermix frequency in excess of 23 Hertz.

In order to convert this circuit to a pain device, the two solenoids 340 and 356 can be connected to a jack, as with the previous pain circuit. Then the jack is connected to a pair of coils as previously described.

This patent specification contains a tremendous amount of background scientific data in support of the embodiments of the present invention set forth herein. It is emphasized that the specific circuit embodiments set forth herein are only one of numerous types of embodiments which are designed to create the resultant effects for both pacing the heart and for counteracting pain.

Described more broadly, the present invention relates to a process for influencing the cardiac function of a human being comprising subjecting an area of the body adjacent to the heart or adjacent to the brain to a cyclic expanding and collapsing magnetic field, said magnetic field comprising a ringing square wave form to produce a Fourier series of harmonics having a fundamental frequency between 7.15 Hertz and 7.78 Hertz, having a duty cycle of from about 15% to about 65% and a field strength of at least 0.5 gauss, and further utilizing the ringing characteristics of the magnetic fields and not introducing smoothing elements so as not to critically dampen the leading and trailing edges of the component ringing square wave pulses to thereby produce a series of pulses which resemble the PQRSTU shape of a heartbeat. In a more precise form, the frequency is specifically set at 7.6 Hertz to create a Fourier series up to about the fifth harmonic at 38 Hertz such that the Fourier series directly contributes to the pacemaking process.

The circuits of the present invention as shown in this specification are further designed to create a process for influencing the cardiac function of a human comprising subjecting an area of the body adjacent to the heart to two cyclic expanding and collapsing magnetic fields; the first cyclic expanding and collapsing magnetic fields comprising a ringing square wave form to produce a Fourier series of harmonics having a fundamental frequency between 7.15 Hertz and 7.78 Hertz, having a duty cycle of from about 15% to about 65% and a field strength of at least 0.5 gauss and further utilizing the ringing characteristics of the magnetic fields and not introducing smoothing elements so as not to critically dampen the leading and trailing edges of the component ringing square wave pulses to thereby produce a series of pulses which resemble the PQRSTU shape of a heartbeat; and the second cyclic expanding and collapsing magnetic field comprising a ringing square wave form to produce a Fourier series of harmonics having a frequency about ten times the fundamental frequency of the first magnetic field, having a field strength of at least 0.5 gauss, and further utilizing the ringing characteristics of the magnetic fields and not introducing smoothing elements so as not to critically dampen the leading and trailing edges of the component ringing square wave pulses to thereby produce a series of pulses which resemble the PQRSTU shape of a heartbeat, and further having a duty cycle of from 15% to 50%, and operating only during the active portion of the duty cycle of the first magnetic field; whereby the dual coils enhance the efficiency of pacing the human heart by increasing the richness of the Fourier components.

Describing the apparatus of the circuits and as supported by this specification, the present invention is also a device for regulating cardiac rhythm comprising a conducting wire coil, a core positioned in said coil, means to produce a flow of electric current through the coil, said flow comprising a ringing square wave form having a fundamental frequency of from about 7.15 Hertz to about 7.78 Hertz and a duty cycle of from about 15% to about 65%, said current flow being sufficient to induce a magnetic field having a strength of at least 0.5 gauss in said core, and means to not introduce smoothing elements so as not to critically dampen the leading and trailing edges of the component ringing square wave pulses to thereby produce a series of pulses which resemble the PQRSTU shape of a heartbeat. In addition, a variation of this embodiment is to have a second means to produce a second flow of electric current which is only active during the active portion of the first means which produces a flow of electric current, the second means to produce a second flow of electric current comprising a ringing square wave form having a fundamental frequency of from about 71.5 Hertz to about 77.8 Hertz and having a duty cycle of about 25%. The core can be an air coil or alternatively can be made of material such as mu-metal. The coil can be a pancake coil. It is beneficial to shield one of the poles of the core so as not to accidentally pace a stranger's heart.

The cardiac pacemaking portion of the present invention also comprises a device for influencing the cardiac function of a human comprising a first conducting wire coil, a core positioned in said coil, first means to produce a flow of electric current through said coil, said flow comprising a ringing square wave form having a fundamental frequency of from about 7.15 Hertz to about 7.78 Hertz and a duty cycle of from about 15% to about 65%, said current flow being sufficient to induce a magnetic field having a strength of at least 0.5 gauss in said core and means to not introduce smoothing elements so as not to critically dampen the leading and trailing edges of the component ringing square wave pulses to thereby produce a series of pulses which resemble the PQRSTU shape of a heartbeat; and a second conducting wire coil, a core positioned in said second conducting wire coil, second means to produce a flow of electric current through said coil, said flow comprising a ringing square wave form having a fundamental frequency of from about 71.5 Hertz to about 77.8 Hertz and a duty cycle of from about 15% to about 65%, said current flow being sufficient to induce a magnetic field having a strength of at least 0.5 gauss in said core and means to not introduce smoothing elements so as not to critically dampen the leading and trailing edges of the component ringing square wave pulses to thereby produce a series of pulses which resemble the PQRSTU shape of a heartbeat; and said first conducting wire coil and said second conducting wire coil being set so that said second conducting wire coil operates only during the active portion of the duty cycle of said first conducting wire coil.

The supporting equations and detailed description of the present invention, in broadest terms, describes a method of pacing the human heart comprising non-invasive coupling of an artificial externally generated magnetic or electric current field with bioexcitable biologic material in vitro or in vivo in order to establish a two-way informational channel between the material, the artificial channel which is in the form of a narrow band highly non-linear frequency modulated system with unique solitary wave-like AM properties to purposefully influence or enhance particularly the optimum functioning of the human brain, nervous and cardiovascular systems and their component and associated parts comprising steps of subjecting appropriate areas of the body to expanding and collapsing magnetic fields of precisely formed shapes and durations with exactly timed intervals which correspond to the resonant mode linear as well as highly non-linear conditions of the given area to be stimulated by the fundamental and odd harmonics of the ringing uncritically damped square waves artificially generated and emitted by coils and/or electrodes as magnetic and electric currents.

The pain control process of the present invention, as illustrated in the aforementioned circuits and supported by this specification can be more broadly described as a process for reducing or extinguishing pain in a human comprising subjecting an area of the body surrounding the focus of the pain to two cyclic expanding and collapsing magnetic fields; the first cyclic expanding and collapsing magnetic field comprising an uncritically damped square wave form to produce a Fourier series of harmonics, having a fundamental frequency between 7.15 Hertz and 7.78 Hertz, having a duty cycle of from about 15% to about 65% and a field strength of at least 5.0 gauss; the second cyclic expanding and collapsing magnetic field comprising an uncritically damped ringing square wave form, having a frequency about ten times the frequency of the first magnetic field to also produce a Fourier series of harmonics, having a field strength of at least 5.0 gauss, and having a duty cycle of from 15% to 50%, and operating simultaneously with the first magnetic field; and said first and second cyclic expanding and collapsing magnetic fields being tuned to each other so that a beat frequency is generated by the dynamic interaction of the two generated frequencies.

As supported by the illustrated circuits and supporting text of the specification, the present invention further involves a device for reducing or extinguishing pain in a human comprising a first conducting wire coil, a core positioned in said coil, first means to produce a flow of electric current through said coil, said flow comprising an uncritically damped ringing square wave form to produce a series of Fourier harmonics having a fundamental frequency of from about 7.15 Hertz to about 7.78 Hertz and a duty cycle of from about 15% to about 65%, and said current flow being sufficient to induce a magnetic field having a strength of at least 5.0 gauss in said core; and a second conducting wire coil, a core positioned in said second conducting wire coil, second means to produce a flow of electric current through said coil, said flow comprising a critically undamped ringing square wave form to produce a series of Fourier harmonics having a fundamental frequency of from about 72.5 Hertz to about 77.8 Hertz and a duty cycle of from about 15% to about 50%, said current flow being sufficient to induce a magnetic field having a strength of at least 5.0 gauss in said core; said first conducting wire coil and said second conducting wire coil being set so that both coils operate simultaneously with 50% duty cycles; and the first and second conducting wire coils being tuned to each other so that the resultant mix of Fourier harmonics produces a beat frequency dynamic interaction of the two generated frequencies. The cores can be made of mu-metal or comparable material or else can be air cores. It is usually advisable to shield one of the poles of each core. The coils can be pancake coils. Alternatively, each of the coils can terminate in an electrode.

When working adjacent the brain (as described for treating dental pain), one should not use magnetic fields. Therefore electrodes can be substituted. In this embodiment of the pain control device, the present invention is a device for reducing or extinguishing pain in a human comprising a first conducting pair of electrodes to form a complete path, first means to produce a flow of electric current through said pair of electrodes, said flow comprising an uncritically damped ringing square wave form to produce a series of Fourier harmonics having a fundamental frequency of from about 7.15 Hertz to about 7.78 Hertz and a duty cycle of from about 15% to about 65%, said current flow being sufficient to induce a voltage of from 5 to 24 volts and a current between 45 to 500 microamperes of current; a second conducting pair of electrodes to form a complete path, second means to produce a flow of electric current through said coil, said flow comprising an uncritically damped ringing square wave form to produce a series of Fourier harmonics having a fundamental frequency of from about 71.5 Hertz to about 77.8 Hertz and a duty cycle of from about 15% to about 50%, said current flow being sufficient to induce a voltage of from 5 to 25 volts and a current between 45 to 500 microamperes of current; said first conducting pair of electrodes and said second conducting pair of electrodes being set so that both pairs of electrodes operate simultaneously with 50% duty cycles; and the first and second pair of electrodes being tuned to each other so that the resultant mix of Fourier harmonics produces a beat frequency dynamic interaction of the two generated frequencies.

Of course the present invention is not intended to be restricted to any particular form or arrangement, or any specific method or embodiment disclosed herein, or any specific use, since the same may be modified in various particulars or relations without departing from the spirit or scope of the claimed invention hereinabove shown and described of which the method and apparatus shown is intended only for illustration and for disclosure of an operative embodiment, and not to show all of the various forms of modification in which the invention might be embodied.

The invention has been described in considerable detail in order to comply with the patent laws by providing a full public disclosure of at least one of its forms. However, such detailed description is not intended in any way to limit the broad features of principles of the invention, or the scope of patent monopoly to be granted.

What is claimed is:

1. A process for reducing pain in a human being comprising:
   a. subjecting an area of the human being's body relating to the locus of the pain to a first cyclic expanding and collapsing magnetic field and a second cyclic expanding and collapsing magnetic field;
   b. said first cyclic expanding and collapsing magnetic field comprising, and uncritically damped ringing square wave form to produce a Fourier series of harmonics having a fundamental frequency between 7 Hertz and 8 Hertz, a duty cycle of from about 15% to about 65%, and a field strength of at least 5.0 gauss;
   c. said second cyclic expanding and collapsing magnetic field comprising, an uncritically damped ringing square wave form having a frequency about ten times the frequency of said first cyclic expanding and collapsing magnetic field to also produce a Fourier series of harmonics, a duty cycle of from about 15% to 50%, a field strength of at least 5.0 gauss, and operating simultaneously with said first cyclic expanding and collapsing magnetic field; and
   d. matching said first cyclic expanding and collapsing magnetic field and said second cyclic expanding and collapsing magnetic field to each other so that a beat frequency is generated by the dynamic interaction of the two generated frequencies;
   e. whereby the beat frequency causes the ion flow in the nervous system of the human body to be efficiently moved along the nerve path where the locus of the pain exists to thereby reduce the pain.

2. The process in accordance with claim 1 wherein said beat frequency is above 23 Hertz.

3. The process in accordance with claim 1 wherein said first cyclic expanding and collapsing magnetic field is an externally produced magnetic field and said second cyclic expanding and collapsing magnetic field is an externally produced magnetic field.

4. The process in accordance with claim 1 further comprising generating broad band random noise in conjunction with said first cyclic expanding and collapsing magnetic field and in conjunction with said second cyclic expanding and collapsing magnetic field to thereby enhance the pain reduction process.

5. A process for reducing pain in a human being comprising:
   a. subjecting an area of the human being's body relating to the locus of the pain to a first cyclic expanding and collapsing electric field and a second cyclic expanding and collapsing electric field;
   b. said first cyclic expanding and collapsing electric field comprising, a ringing square wave form to produce a Fourier series of harmonics having a fundamental frequency between 7 Hertz and 8 Hertz, a duty cycle of from about 15% to about 65%, and an RMS voltage of at least 5 to 24 volts and a current at least between 45 to 500 microamperes;
   c. said second cyclic expanding and collapsing electric field comprising, a ringing square wave form having a frequency about ten times the frequency of said first cyclic expanding and collapsing electric field to also produce a Fourier series of harmonics, a duty cycle of from about 15% to 50%, and an RMS voltage of at least 5 to 24 volts and a current at least between 45 to 500 microamperes; and
   d. matching said first cyclic expanding and collapsing electric field and said second cyclic expanding and collapsing electric field to each other so that a beat frequency is generated by the dynamic interaction of the two generated frequencies;
   e. whereby the beat frequency causes the ion flow in the nervous system of the human body to be efficiently moved along the nerve path where the locus of the pain exists to thereby reduce the pain.

6. The process in accordance with claim 5 wherein said beat frequency is above 23 Hertz.

7. The process in accordance with claim 5 wherein said first cyclic expanding and collapsing electric field is an electric field which is cutaneously applied to the human being and said second cyclic expanding and collapsing electric field is an electric field which is cutaneously applied to the human being.

8. A process for reducing pain in a human being comprising:
   a. subjecting an area of the human being's body relating to the locus of the pain to a first cyclic expanding and collapsing magnetic field and a second cyclic expanding and collapsing electric field;
   b. said first cyclic expanding and collapsing magnetic field comprising, an uncritically damped ringing square wave form to produce a Fourier series of harmonics, a fundamental frequency between 7 Hertz and 8 Hertz, a duty cycle of from about 15% to about 65%, and a field strength of at least 5.0 gauss;
   c. said second cyclic expanding and collapsing electric field comprising, a ringing square wave form having a frequency about ten times the frequency of said first cyclic expanding and collapsing magnetic field to also produce a Fourier series of harmonics, a duty cycle of from about 15% to 50%, an RMS voltage of at least 5 to 24 volts and a current at least between 45 to 500 microamperes, and operating simultaneously with said first cyclic expanding and collapsing magnetic field; and
   d. matching said first cyclic expanding and collapsing magnetic field and said second cyclic expanding and collapsing electric field to each other so that a beat frequency is generated by the dynamic interaction of the two generated frequencies;
   e. whereby the beat frequency causes the ion flow in the nervous system of the human body to be efficiently moved along the nerve path where the locus of the pain exists to thereby reduce the pain.

9. The process in accordance with claim 8 wherein said beat frequency is about 23 Hertz.

10. The process in accordance with claim 8 wherein said first cyclic expanding and collapsing magnetic field is an externally produced magnetic field and said second cyclic expanding and collapsing electric field is an electric field which is cutaneously applied to the human being.

11. The process in accordance with claim 8 further comprising generating broad band random noise in conjunction with said first cyclic expanding and collapsing magnetic field to thereby enhance the pain reduction process.

12. A process for reducing pain in a human being comprising:
   a subjecting an area of the human being's body relating to the locus of the pain to a first cyclic expanding and collapsing electric field and a second cyclic expanding and collapsing magnetic field;
   b. said first cyclic expanding and collapsing electric field comprising, a ringing square wave form to produce a Fourier series of harmonics having a fundamental frequency between 7 Hertz and 8 Hertz, a duty cycle of from about 15% to about 65%, and an RMS voltage of at least 5 to 24 volts and a current at least between 45 to 500 microamperes;
   c. said second cyclic expanding and collapsing magnetic field comprising, an uncritically damped ringing square wave form having a frequency about ten times the frequency of said first cyclic expanding and collapsing electric field to also produce a Fourier series of harmonics, a duty cycle of from about 15% to 50%, and RMS voltage of at least 5 to 24 volts and a current at least between 45 to 500 microamperes, and operating simultaneously with said first cyclic expanding and collapsing electric field; and
   d. matching said first cyclic expanding and collapsing electric field and said second cyclic expanding and collapsing magnetic field to each other so that a beat frequency is generated by the dynamic interaction of the two generated frequencies;
   e. whereby the beat frequency causes the ion flow in the nervous system of the human body to be efficiently moved along the nerve path where the locus of the pain exists to thereby reduce the pain.

13. The process in accordance with claim 12 wherein said beat frequency is above 23 Hertz.

14. The process in accordance with claim 12 wherein said first cyclic expanding and collapsing electric field is an electric field which is cutaneously applied to the human being and said second cyclic expanding and collapsing magnetic field is an externally produced magnetic field.

15. The process in accordance with claim 12 further comprising generating broad band random noise in conjunction with said second cyclic expanding and collapsing magnetic field to thereby enhance the pain reduction process.

16. A device for reducing pain in a human being comprising:
   a. a first conducting wire coil;
   b. a first core positioned in said first conducting wire coil;
   c. a second conducting wire coil in parallel with said first conducting wire coil;
   d. a second core positioned in said second conducting wire coil;
   e. a first means to simultaneously produce a flow of electric current through said first conducting wire coil and said second conducting wire coil, said flow comprising, an uncritically damped ringing square wave form to produce a series of Fourier harmonics having a fundamental frequency of from about 7 Hertz to about 8 Hertz, a duty cycle of from about 15% to about 65%, said current flow being sufficient to induce a magnetic field having a strength of at least 5.0 gauss in said first core and in a said second core;
   f. a second means to simultaneously produce a flow of electric current through said first conducting wire coil and second conducting wire coil, said flow comprising, an uncritically damped ringing square wave form to produce a series of Fourier harmonics having a fundamental frequency about ten times the frequency generated by said first means, a duty cycle of from about 15% to about 50%, said current flow being sufficient to induce a magnetic field having a strength of at least 5.0 gauss in said first core and in said second core;
   g. the first means to produce a flow of electric current and the second means to produce a flow of electric current being set to operate simultaneously so that said first conducting wire coil and said second conducting wire coil operate simultaneously; and
   h. the first means to produce a flow of electric current and the second means to produce a flow of electric current being tuned to each other so that the resultant mix of Fourier harmonics produces a beat frequency dynamic interaction of the two generated frequencies;

i. whereby when said device is focused on an area of a human body relating to a locus of pain, the beat frequency causes the ion flow in the nervous system of the human body to be efficiently moved along the nerve path where the locus of the pain exists to thereby reduce the pain.

17. A device for reducing pain in a human being comprising:

a. at least one conducting wire coil;

b. a core positioned in said at least one conducting wire coil;

c. a first means to produce a flow of electric current through said at least one conducting wire coil, said flow comprising, an uncritically damped ringing square wave form to produce a series of Fourier harmonics having a fundamental frequency of from about 7 Hertz to about 8 Hertz, a duty cycle of from about 15% to about 65%, said current flow being sufficient to induce a magnetic field having a strength of at least 5.0 gauss in said core;

d. a second means to simultaneously produce a flow of electric current through said at least one conducting wire coil, said flow comprising, an uncritically damped ringing square wave form to produce a series of Fourier harmonics having a fundamental frequency about ten times the frequency generated by said first means to produce a flow of electric current, a duty cycle of from about 15% to about 50%, said current flow being sufficient to induce a magnetic field having a strength of at least 5.0 gauss in said core;

e. the first means to produce a flow of electric current and the second means to produce a flow of electric current being set to operate simultaneously in said at least one conducting wire coil; and f. said first means to produce a flow of electric current and said second means to produce a flow of electric current being tuned to each other so that the resultant mix of Fourier harmonics produces a beat frequency dynamic interaction of the two generated frequencies.

g. whereby when said device is focused on an area of a human body relating to a locus of pain, the beat frequency causes the ion flow in the nervous system of the human body to be efficiently moved along the nerve path where the locus of the pain exists to thereby reduce the pain.

18. A device for reducing pain in a human being comprising:

a first conducting pair of electrodes which form a complete current path;

b. a second conducting pair of electrodes which form a complete current path;

c. a first means to simultaneously produce a flow of electric current through said first conducting pair of electrodes and said second conducting pair of electrodes, said flow comprising, a ringing square wave form to produce a series of Fourier harmonics having a fundamental frequency of from about 7 Hertz to about 8 Hertz, a duty cycle of from about 15% to about 65%, said current flow being sufficient to induce an RMS voltage of at least 5 to 24 volts and a current at least between 45 to 500 microamperes;

d. a second means to simultaneously produce a flow of electric current through said first conducting pair of electrodes and said second conducting pair of electrodes, said flow comprising, a ringing square wave form to produce a series of Fourier harmonics having a fundamental frequency about 10 times the frequency produced by said first means to produce a flow of electric current, a duty cycle of from about 15% to about 50%, said current flow being sufficient to induce an RMS voltage of at least 5 to 24 volts and a current at least between 45 to 500 microamperes of current;

e. the first means to produce a flow of electric current and the second means to produce a flow of electric current being set to operate simultaneously; and f. the first means to produce a flow of electric current and the second means to produce a flow of electric current being tuned to each other so that the resultant mix of Fourier harmonics produces a beat frequency dynamic interaction of the two generated frequencies;

g. whereby when said device is focused on an area of a human body where there is a locus of pain, the beat frequency causes the ion flow in the nervous system of the human body to be efficiently moved along the nerve path where the locus of the pain exists to thereby reduce the pain.

19. A device for reducing pain in a human being comprising:

a. at least one conducting pair of electrodes which form a complete current path;

b. a first means to produce a flow of electric current through said at least one conducting pair of electrodes, said flow comprising, a ringing square wave form to produce a series of Fourier harmonics having a fundamental frequency of from about 7 Hertz to about 8 Hertz, a duty cycle of from about 15% to about 65%, said current flow being sufficient to induce an RMS voltage of at least 5 to 24 volts and a current at least between 45 to 500 microamperes of current;

c. a second means to simultaneously produce a flow of electric current through said at least one conducting pair of electrodes, said flow comprising, a ringing square wave form to produce a series of Fourier harmonics having a fundamental frequency about 10 times the frequency produces by said first means to produce a flow of electric current, a duty cycle of from about 15% to about 50%, said current flow being sufficient to induce an RMS voltage of at least 5 to 24 volts and a current at least between 45 to 500 microamperes of current;

d. the first means to produce a flow of electric current and the second means to produce a flow of electric current being set to operate simultaneously; and e. said first means to produce a flow of electric current and said second means to produce a flow of electric current being tuned to each other so that the resultant mix of Fourier harmonics produces a beat frequency dynamic interaction of the two generated frequencies;

f. whereby when said device is focused on an area of a human body where there is a locus of pain, the beat frequency causes the ion flow in the nervous system of the human body to be efficiently moved along the nerve path where the locus of the pain exists to thereby reduce the pain.

20. A device for reducing pain in a human being comprising:

a. at least one conducting wire coil;

b. a core positioned in said at least one conducting wire coil;

c. at least one conducting pair electrodes which form a complete current path;
d. a first means to simultaneously produce a flow of electric current through said at least one conducting wire coil and said at least one conducting pair of electrodes, said flow comprising, an uncritically damped ringing square wave form to produce a series of Fourier harmonics having a fundamental frequency of from about 7 Hertz to about 8 Hertz, a duty cycle of from about 15% to about 65%, said current flow being sufficient to induce a magnetic field having a strength of at least 5.0 gauss in said core and an RMS voltage of at least 5 to 24 volts and a current at least between 45 to 500 microamperes in said at least one conducting pair of electrodes;
e. a second means to simultaneously produce a flow of electric current through said at least one conducting wire coil and said at least one conducting pair of electrodes, said flow comprising, an uncritically damped ringing square wave form to produce a series of Fourier harmonics having a fundamental frequency about 10 times the frequency produced by said first means to produce a flow of electric current, a duty cycle of from about 15% to about 50%, said current flow being sufficient to induce a magnetic field having a strength of at least 5.0 gauss in said core and an RMS voltage of at least 5 to 24 volts and a current at least between 45 to 500 microamperes in said at least one conducting pair of electrodes;
f. the first means to produce a flow of electric current and the second means to produce a flow of electric current being set to operate simultaneously; and
g. the first means to produce a flow of electric current and the second means to produce a flow of electric current being tuned to each other so that the resultant mix of Fourier harmonics produces a beat frequency dynamic interaction of the two generated frequencies;
h. whereby when said device is focused on an area of a human body relating to a locus of pain, the beat frequency causes the ion flow in the nervous system of the human body to be efficiently moved along the nerve path where the locus of the pain exists to thereby reduce the pain.

* * * * *